US010934598B2

(12) United States Patent
Carrick

(10) Patent No.: US 10,934,598 B2
(45) Date of Patent: Mar. 2, 2021

(54) ASSAY FOR DETECTION OF HUMAN PARVOVIRUS NUCLEIC ACID

(71) Applicant: GEN-PROBE INCORPORATED, San Diego, CA (US)

(72) Inventor: James M. Carrick, Lanham, MD (US)

(73) Assignee: GEN-PROBE INCORPORATED, San Diego, CA (US)

( * ) Notice: Subject to any disclaimer, the term of this patent is extended or adjusted under 35 U.S.C. 154(b) by 337 days.

(21) Appl. No.: 16/013,502

(22) Filed: Jun. 20, 2018

(65) Prior Publication Data
US 2018/0347000 A1 Dec. 6, 2018

Related U.S. Application Data

(60) Division of application No. 14/569,338, filed on Dec. 12, 2014, now Pat. No. 10,087,494, which is a continuation of application No. 13/203,715, filed as application No. PCT/US2010/025499 on Feb. 26, 2010, now Pat. No. 8,921,039.

(60) Provisional application No. 61/155,685, filed on Feb. 26, 2009.

(51) Int. Cl.
*C12Q 1/68* (2018.01)
*C12Q 1/70* (2006.01)
*C12Q 1/686* (2018.01)

(52) U.S. Cl.
CPC ............ *C12Q 1/701* (2013.01); *C12Q 1/702* (2013.01); *C12Q 1/686* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,399,491 A | 3/1995 | Kacian et al. |
| 5,622,827 A | 4/1997 | McAllister et al. |
| 6,214,555 B1 | 4/2001 | Leushner et al. |
| 6,274,307 B1 | 8/2001 | Soutschek et al. |
| 6,936,442 B2 | 8/2005 | Pichuantes et al. |
| 7,094,541 B2 * | 8/2006 | Brentano ............... C12Q 1/701 435/6.18 |
| 7,291,452 B1 | 11/2007 | Nguyen et al. |
| 8,198,027 B2 | 6/2012 | Brentano et al. |
| 2002/0068694 A1 | 6/2002 | Jeltsch et al. |
| 2003/0119016 A1 | 6/2003 | Riley et al. |
| 2006/0008469 A1 | 1/2006 | Brown et al. |
| 2006/0014142 A1 | 1/2006 | Carlson et al. |
| 2006/0057643 A1 | 3/2006 | McCarthy et al. |
| 2006/0121516 A1 | 6/2006 | Norman et al. |
| 2008/0311155 A1 | 12/2008 | Nicolette et al. |

FOREIGN PATENT DOCUMENTS

| | | |
|---|---|---|
| WO | 99/28439 A2 | 6/1999 |
| WO | 01/06019 A2 | 1/2001 |
| WO | 03/020742 A1 | 3/2003 |
| WO | 2006/007603 A2 | 1/2006 |
| WO | 2007/096199 A2 | 8/2007 |
| WO | 2008/089193 A2 | 7/2008 |
| WO | 2010/099378 A3 | 9/2010 |

OTHER PUBLICATIONS

Hemauer et al. (J Gen Virol, 1996, 77, p. 1781-1785) (Year: 1996).*
Lowe et al. (Nucleic Acids Research, 1990, 18(7):1757-1761) (Year: 1990).*
USPTO Non-Final Rejection, U.S. Appl. No. 13/203,715, dated Nov. 21, 2013.
USPTO Final Rejection, U.S. Appl. No. 13/203,715, dated May 22, 2014.
USPTO Advisory Action, U.S. Appl. No. 13/203,715, dated Jun. 19, 2014.
USPTO Notice of Allowance & Examiner-Initiated Interview Summary, U.S. Appl. No. 13/203,715, dated Aug. 27, 2014.
USPTO Non-Final Rejection, U.S. Appl. No. 14/569,338, dated Sep. 22, 2017.
USPTO Final Rejection, U.S. Appl. No. 14/569,338, dated Apr. 10, 2018.
USPTO Notice of Allowance, U.S. Appl. No. 14/569,338, dated May 31, 2018.
APO Examiner's First Report, Australian Application No. 2010217928, dated Jun. 4, 2012.
APO Notice of Acceptance, Australian Application No. 2010217928, dated May 23, 2013.
CIPO Exam Report, Canadian Application No. 2,756,659, dated Sep. 7, 2012.
EPO Communication pursuant to Article 94(3), European Application No. 10746873.8, dated Feb. 19, 2015.
EPO Extended European Search Report, European Application No. 16183806.5, dated Dec. 9, 2016.
EPO Extended European Search Report, European Application No. 17181037.7, dated Nov. 8, 2017.
PCT International Preliminary Report on Patentability, International Application No. PCT/US2010/025499, dated Aug. 30, 2011.
PCT Written Opinion, International Application No. PCT/US2010/025499, dated Aug. 9, 2010.
PCT International Search Report, International Application No. PCT/US2010/025499, dated Aug. 9, 2010.
USPTO Non-Final Rejection, U.S. Appl. No. 10/231,843, dated Aug. 30, 2005.

(Continued)

*Primary Examiner* — Stephanie K Mummert
(74) *Attorney, Agent, or Firm* — Nicholas V. Sherbina; Jeffrey E. Landes

(57) ABSTRACT

Nucleic acid oligomers specific for human parvovirus genomic DNA are disclosed. An assay for amplifying and detecting human parvovirus genotypes 1, 2 and 3 nucleic acid in biological specimens is disclosed. Compositions for amplifying and detecting the presence of human parvovirus genotypes 1, 2 and 3 genomic DNA in human biological specimens are disclosed.

19 Claims, No Drawings

Specification includes a Sequence Listing.

(56) References Cited

OTHER PUBLICATIONS

USPTO Notice of Allowance, U.S. Appl. No. 10/231,843, dated Mar. 20, 2006.
USPTO Non-Final Rejection, U.S. Appl. No. 11/459,908, dated Jul. 6, 2009.
USPTO Non-Final Rejection, U.S. Appl. No. 11/459,908, dated Jan. 15, 2010.
USPTO Final Rejection, U.S. Appl. No. 11/459,908, dated Jul. 20, 2010.
USPTO Non-Final Rejection, U.S. Appl. No. 11/459,908, dated Dec. 27, 2010.
USPTO Final Rejection, U.S. Appl. No. 11/459,908, dated Jun. 9, 2011.
USPTO Notice of Allowance, U.S. Appl. No. 11/458,908, dated Oct. 9, 2012.
PCT International Search report, International Application No. PCT/US02/27734, dated Jan. 10, 2003.
Aberham et al., "A quantitative, internally controlled real-time PCR assay for the detection of parvovirus B19 DNA," Journal of Virological Methods, 2001, 92(2):183-191, Elsevier Science, Amsterdam, Netherlands.
Diss et al., "Parvovirus B19 is associated with benign testes as well as testicular germ cell tumors," J. Clin. Pathol.: Mol. Pathol., 1999, 52:349-352, Association of Clinical Pathologists, London, United Kingdom.
Durigon et al., "Multiple primer pairs for polymerase chain reaction (PCR) amplification of human parvovirus B19 DNA," Journal of Virological Methods, 1993, 44:155-165.
Ekman et al., "Biological and Immunological Relations among Human Parvovirus B19 Genotypes 1 to 3," J. Virol., 2007, 81(13):6927-6935, American Society for Microbiology, Washington D.C., USA.
Database GenEmbl, Accession No. AF380251, Sol-Church et al. "B19 virus isolate 7 VP1 protein gene, partial cds," Jun. 2001.
Genbank Data Entry: No. DQ225149.1, Version No. DQ225149.1, "Human parvovirus B19 isolate SN807 non-structural protein (NS1), 7.5 kDa protein, minor capsid protein (VP1), 9.5 kDa prtein, and major capsid protein (VP2) genes, complete cds,", Sep. 12, 2006.
Database GenEmbl, Accession No. Z70533, Hemauer et al. "Parvovirus B19 DNA, patient 3, genome position 2647-2939," Nov. 15, 1996.
Database GenEmbl, Accession No. Z70591, Hemauer et al. "Parvovirus B19 DNA, patient S724, genome position 2448-2977," Apr. 9, 1996.
Johansen et al., "Typing of European strains of parvovirus B19 by restriction endonuclease analyses and sequencing: identification of evolutionary lineages and evidence of recombination of markers from different lineages," Virus Research, 1998, 53:215-223, Elsevier Science, Amsterdam, Netherlands.
Lefrere et al., "Albumin batches and B19 parvovirus DNA," Transfusion, 1995, 53(5):389-391, American Association of Blood Banks, Bethesda, USA.
Lowe et al., "A computer program for selection of oligonucleotide primers for polymerase chain reactions," Nucleic Acids Research, 18(7):1757-1761.
Takahashi et al., "Genetic heterogeneity of the immunogenic viral capsid protein region of human parvovirus B19 isolates obtained from an outbreak in a pediatric ward," FEBS Letter, 1999, p. 289-293.
Tereshko et al., "Correlating Structure and Stability of DNA Duplexes with Incorporated 2'-0-Modified RNA Analogues," Biochemistry, 1998, 37:10626-10634.
Schowengerdt et al., "Association of parvovirus B19 genome in children with myocarditis and cardiac allograft rejection," Circulation, 1997, 96(10):3549-3554, American Heart Association, Dallas, USA.
Servant et al., "Genetic Diversity within Human Erythroviruses: Identification of Three Genotypes," J. Virol., 2002, 76(18):9124-9134, American Society for Microbiology, Washington D.C., USA.
"A Comparison of a Commercial and in-House Assay," Sanquin, SoGAT, Mar. 2007.
"Commercial Assay and Detection of Parvovirus B19 Genotypes," Sally A. Baylis, NIBSC Division of Virology, SoGAT, Mar. 2007.
"Experience in Testing of Genotypes of B19," Talecris Biotherapeutics, Extraordinary SoGAT meeting on B19, Mar. 2, 2007.
"Experience with In-House Assay: Validation of an In-House NAT Assay for the Detection of Different Genotypes of vB19," Marta Jose, GRIFOLS, SoGAT Standardization of Parvovirus B19 Genotypes, Mar. 2007.
Umene et al., "Genetic diversity of human parvovirus B19 determined using a set of restriction endonucleases recognizing four of rive base pairs and partial nucleotide sequencing: use of sequence variability in virus classification," Journal of General Virology, 1991, 72(8):1997-2001, Society for General Microbiology, London, United Kingdom.

\* cited by examiner

SEQUENCE LISTING

```
<160> NUMBER OF SEQ ID NOS: 100

<210> SEQ ID NO 1
<211> LENGTH: 28
<212> TYPE: DNA
<213> ORGANISM: Artificial Sequence
<220> FEATURE:
<223> OTHER INFORMATION: synthetic oligomer

<400> SEQUENCE: 1
gttggctata cctaaagtca tgaatcct                                       28

<210> SEQ ID NO 2
<211> LENGTH: 32
<212> TYPE: DNA
<213> ORGANISM: Artificial Sequence
<220> FEATURE:
<223> OTHER INFORMATION: synthetic oligomer

<400> SEQUENCE: 2
gccagttggc tatacctaaa gtcatgaatc ct                                  32

<210> SEQ ID NO 3
<211> LENGTH: 53
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 3
aatttaatac gactcactat agggagacta ggttctgcat gactgctact gga           53

<210> SEQ ID NO 4
<211> LENGTH: 26
```

-continued

<212> TYPE: DNA
<213> ORGANISM: Artificial Sequence
<220> FEATURE:
<223> OTHER INFORMATION: synthetic oligomer

<400> SEQUENCE: 4
ctaggttctg catgactgct actgga                                          26

<210> SEQ ID NO 5
<211> LENGTH: 53
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 5
aatttaatac gactcactat agggagactg catgactgct actggatgat aag            53

<210> SEQ ID NO 6
<211> LENGTH: 26
<212> TYPE: DNA
<213> ORGANISM: Artificial Sequence
<220> FEATURE:
<223> OTHER INFORMATION: synthetic oligomer

<400> SEQUENCE: 6
ctgcatgact gctactggat gataag                                          26

<210> SEQ ID NO 7
<211> LENGTH: 56
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 7
aatttaatac gactcactat agggagacta ggttctgcat gactgctact ggatga         56

<210> SEQ ID NO 8
<211> LENGTH: 29
<212> TYPE: DNA
<213> ORGANISM: Artificial Sequence
<220> FEATURE:
<223> OTHER INFORMATION: synthetic oligomer

<400> SEQUENCE: 8
ctaggttctg catgactgct actggatga                                       29

<210> SEQ ID NO 9
<211> LENGTH: 52
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 9
aatttaatac gactcactat agggagagtt ctgcatgact gctactggat ga          52

<210> SEQ ID NO 10
<211> LENGTH: 25
<212> TYPE: DNA
<213> ORGANISM: Artificial Sequence
<220> FEATURE:
<223> OTHER INFORMATION: synthetic oligomer

<400> SEQUENCE: 10
gttctgcatg actgctactg gatga                                        25

<210> SEQ ID NO 11
<211> LENGTH: 53
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 11
aatttaatac gactcactat agggagattc tcctctaggt tctgcatgac tgc          53

<210> SEQ ID NO 12
<211> LENGTH: 26
<212> TYPE: DNA
<213> ORGANISM: Artificial Sequence
<220> FEATURE:
<223> OTHER INFORMATION: synthetic oligomer

<400> SEQUENCE: 12
ttctcctcta ggttctgcat gactgc                                       26

<210> SEQ ID NO 13
<211> LENGTH: 21
<212> TYPE: DNA
<213> ORGANISM: Artificial Sequence
<220> FEATURE:
<223> OTHER INFORMATION: synthetic oligomer

<400> SEQUENCE: 13
cccctagaaa acccatcctc t                                            21

<210> SEQ ID NO 14
<211> LENGTH: 29
<212> TYPE: DNA
<213> ORGANISM: Artificial Sequence
<220> FEATURE:
<223> OTHER INFORMATION: synthetic oligomer

<400> SEQUENCE: 14
ctctccagac ttatatagtc atcattttc                                    29

<210> SEQ ID NO 15
<211> LENGTH: 25
<212> TYPE: DNA
<213> ORGANISM: Artificial Sequence
<220> FEATURE:
<223> OTHER INFORMATION: synthetic oligomer

<400> SEQUENCE: 15
ctctccagac ttatatagtc atcat                                        25

```
<210> SEQ ID NO 16
<211> LENGTH: 23
<212> TYPE: DNA
<213> ORGANISM: Artificial Sequence
<220> FEATURE:
<223> OTHER INFORMATION: synthetic oligomer

<400> SEQUENCE: 16
atcccctaga aacccatcc tct                                               23

<210> SEQ ID NO 17
<211> LENGTH: 25
<212> TYPE: DNA
<213> ORGANISM: Artificial Sequence
<220> FEATURE:
<223> OTHER INFORMATION: synthetic oligomer

<400> SEQUENCE: 17
gacagttatc tgaccacccc catgc                                            25

<210> SEQ ID NO 18
<211> LENGTH: 22
<212> TYPE: DNA
<213> ORGANISM: Artificial Sequence
<220> FEATURE:
<223> OTHER INFORMATION: synthetic oligomer

<400> SEQUENCE: 18
catggacagt tatctgacca cc                                               22

<210> SEQ ID NO 19
<211> LENGTH: 27
<212> TYPE: DNA
<213> ORGANISM: Artificial Sequence
<220> FEATURE:
<223> OTHER INFORMATION: Synthetic Oligomer - Promoter Sequence

<400> SEQUENCE: 19
aatttaatac gactcactat agggaga                                          27

<210> SEQ ID NO 20
<211> LENGTH: 27
<212> TYPE: DNA
<213> ORGANISM: Artificial Sequence
<220> FEATURE:
<223> OTHER INFORMATION: synthetic oligomer

<400> SEQUENCE: 20
catcactttc ccaccatttg ccactttt                                         27

<210> SEQ ID NO 21
<211> LENGTH: 32
<212> TYPE: DNA
<213> ORGANISM: Artificial Sequence
<220> FEATURE:
<223> OTHER INFORMATION: synthetic oligomer

<400> SEQUENCE: 21
gcaaatttat catcactttc ccaccatttg cc                                    32

<210> SEQ ID NO 22
<211> LENGTH: 28
<212> TYPE: DNA
<213> ORGANISM: Artificial Sequence
<220> FEATURE:
<223> OTHER INFORMATION: Synthetic Oligomer or residues 2505 to 2532 of
      SEQ ID NO:90
```

<400> SEQUENCE: 22
aggattcatg actttaggta tagccaac        28

<210> SEQ ID NO 23
<211> LENGTH: 52
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 23
aatttaatac gactcactat agggagaagt accgggtagt tgtacgctaa ct        52

<210> SEQ ID NO 24
<211> LENGTH: 25
<212> TYPE: DNA
<213> ORGANISM: Artificial Sequence
<220> FEATURE:
<223> OTHER INFORMATION: synthetic oligomer

<400> SEQUENCE: 24
agtaccgggt agttgtacgc taact        25

<210> SEQ ID NO 25
<211> LENGTH: 82
<212> TYPE: DNA
<213> ORGANISM: Artificial Sequence
<220> FEATURE:
<223> OTHER INFORMATION: Synthetic Oligomer

<400> SEQUENCE: 25
cttatcatcc agtaacagtc atgcagaacc tagaggagaa aatgcagtat tatctagtga        60
agacttacac aagcctgggc aa        82

<210> SEQ ID NO 26
<211> LENGTH: 107
<212> TYPE: DNA
<213> ORGANISM: Artificial Sequence
<220> FEATURE:
<223> OTHER INFORMATION: Synthetic Oligomer

<400> SEQUENCE: 26
gacagttatc tgaccacccc catgccttat catccagtaa cagtcatgca gaacctagag        60
gagaaaatgc agtattatct agtgaagact tacacaagcc tgggcaa        107

<210> SEQ ID NO 27
<211> LENGTH: 20
<212> TYPE: DNA
<213> ORGANISM: Artificial Sequence
<220> FEATURE:
<223> OTHER INFORMATION: synthetic oligomer

<400> SEQUENCE: 27
gtcatggaca gttatctgac        20

<210> SEQ ID NO 28
<211> LENGTH: 22
<212> TYPE: DNA
<213> ORGANISM: Artificial Sequence
<220> FEATURE:

<223> OTHER INFORMATION: Synthetic Oligomer

<400> SEQUENCE: 28
gtattatcta gtgaagactt ac                                         22

<210> SEQ ID NO 29
<211> LENGTH: 37
<212> TYPE: DNA
<213> ORGANISM: Artificial Sequence
<220> FEATURE:
<223> OTHER INFORMATION: Synthetic Oligomer or residues 2065 to 2101 of
      SEQ ID NO:90

<400> SEQUENCE: 29
aaagtggcaa atggtgggaa agtgatgata aatttgc                         37

<210> SEQ ID NO 30
<211> LENGTH: 21
<212> TYPE: DNA
<213> ORGANISM: Artificial Sequence
<220> FEATURE:
<223> OTHER INFORMATION: synthetic oligomer

<400> SEQUENCE: 30
ctagtgaaga cttacacaag c                                          21

<210> SEQ ID NO 31
<211> LENGTH: 21
<212> TYPE: DNA
<213> ORGANISM: Artificial Sequence
<220> FEATURE:
<223> OTHER INFORMATION: synthetic oligomer

<400> SEQUENCE: 31
gtgaagactt acacaagcct g                                          21

<210> SEQ ID NO 32
<211> LENGTH: 21
<212> TYPE: DNA
<213> ORGANISM: Artificial Sequence
<220> FEATURE:
<223> OTHER INFORMATION: synthetic oligomer

<400> SEQUENCE: 32
gcagtattat ctagtgaaga c                                          21

<210> SEQ ID NO 33
<211> LENGTH: 34
<212> TYPE: DNA
<213> ORGANISM: Artificial Sequence
<220> FEATURE:
<223> OTHER INFORMATION: Synthetic Oligomer or residues 2376 to 2409 of
      SEQ ID NO:90

<400> SEQUENCE: 33
gcagtattat ctagtgaaga cttacacaag cctg                            34

<210> SEQ ID NO 34
<211> LENGTH: 22
<212> TYPE: RNA
<213> ORGANISM: Artificial Sequence
<220> FEATURE:
<223> OTHER INFORMATION: synthetic oligomer

<400> SEQUENCE: 34
caaagucaug gacaguuauc ug                                         22

```
<210> SEQ ID NO 35
<211> LENGTH: 35
<212> TYPE: DNA
<213> ORGANISM: Artificial Sequence
<220> FEATURE:
<223> OTHER INFORMATION: Synthetic Oligomer or residues 2298 to 2332 of
      SEQ ID NO:90

<400> SEQUENCE: 35
caaagtcatg gacagttatc tgaccacccc catgc                              35

<210> SEQ ID NO 36
<211> LENGTH: 20
<212> TYPE: DNA
<213> ORGANISM: Artificial Sequence
<220> FEATURE:
<223> OTHER INFORMATION: synthetic oligomer

<400> SEQUENCE: 36
ctgtttgact tagttgctcg                                               20

<210> SEQ ID NO 37
<211> LENGTH: 25
<212> TYPE: RNA
<213> ORGANISM: Artificial Sequence
<220> FEATURE:
<223> OTHER INFORMATION: synthetic oligomer

<400> SEQUENCE: 37
cucuccagac uuauauaguc aucau                                         25

<210> SEQ ID NO 38
<211> LENGTH: 18
<212> TYPE: DNA
<213> ORGANISM: Artificial Sequence
<220> FEATURE:
<223> OTHER INFORMATION: Synthetic Oligomer or residues 2302 to 2319 of
      SEQ ID NO:90

<400> SEQUENCE: 38
gtcatggaca gttatctg                                                 18

<210> SEQ ID NO 39
<211> LENGTH: 18
<212> TYPE: DNA
<213> ORGANISM: Artificial Sequence
<220> FEATURE:
<223> OTHER INFORMATION: synthetic oligomer

<400> SEQUENCE: 39
gtgaagactt acacaagc                                                 18

<210> SEQ ID NO 40
<211> LENGTH: 18
<212> TYPE: DNA
<213> ORGANISM: Artificial Sequence
<220> FEATURE:
<223> OTHER INFORMATION: Synthetic Oligomer or residues 2379 to 2396 of
      SEQ ID NO:90

<400> SEQUENCE: 40
gtattatcta gtgaagac                                                 18

<210> SEQ ID NO 41
<211> LENGTH: 22
```

```
<212> TYPE: DNA
<213> ORGANISM: Artificial Sequence
<220> FEATURE:
<223> OTHER INFORMATION: synthetic oligomer

<400> SEQUENCE: 41
catcactttc ccaccatttg cc                                              22

<210> SEQ ID NO 42
<211> LENGTH: 22
<212> TYPE: RNA
<213> ORGANISM: Artificial Sequence
<220> FEATURE:
<223> OTHER INFORMATION: Synthetic Oligomer

<400> SEQUENCE: 42
guauuaucua gugaagacuu ac                                              22

<210> SEQ ID NO 43
<211> LENGTH: 21
<212> TYPE: RNA
<213> ORGANISM: Artificial Sequence
<220> FEATURE:
<223> OTHER INFORMATION: synthetic oligomer

<400> SEQUENCE: 43
cuagugaaga cuuacacaag c                                               21

<210> SEQ ID NO 44
<211> LENGTH: 21
<212> TYPE: RNA
<213> ORGANISM: Artificial Sequence
<220> FEATURE:
<223> OTHER INFORMATION: synthetic oligomer

<400> SEQUENCE: 44
gugaagacuu acacaagccu g                                               21

<210> SEQ ID NO 45
<211> LENGTH: 22
<212> TYPE: DNA
<213> ORGANISM: Artificial Sequence
<220> FEATURE:
<223> OTHER INFORMATION: synthetic oligomer

<400> SEQUENCE: 45
caaagtcatg gacagttatc tg                                              22

<210> SEQ ID NO 46
<211> LENGTH: 21
<212> TYPE: RNA
<213> ORGANISM: Artificial Sequence
<220> FEATURE:
<223> OTHER INFORMATION: synthetic oligomer

<400> SEQUENCE: 46
gcaguauuau cuagugaaga c                                               21

<210> SEQ ID NO 47
<211> LENGTH: 45
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(20)
```

```
<223> OTHER INFORMATION: tag sequence

<400> SEQUENCE: 47
gtcatatgcg acgatctcag gacagttatc tgaccacccc catgc                45

<210> SEQ ID NO 48
<211> LENGTH: 25
<212> TYPE: DNA
<213> ORGANISM: Artificial Sequence
<220> FEATURE:
<223> OTHER INFORMATION: synthetic oligomer

<400> SEQUENCE: 48
gacagttatc tgaccacccc catgc                                      25

<210> SEQ ID NO 49
<211> LENGTH: 38
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(20)
<223> OTHER INFORMATION: tag sequence

<400> SEQUENCE: 49
gtcatatgcg acgatctcag gacagttatc tgaccacc                        38

<210> SEQ ID NO 50
<211> LENGTH: 18
<212> TYPE: DNA
<213> ORGANISM: Artificial Sequence
<220> FEATURE:
<223> OTHER INFORMATION: synthetic oligomer

<400> SEQUENCE: 50
gacagttatc tgaccacc                                              18

<210> SEQ ID NO 51
<211> LENGTH: 23
<212> TYPE: DNA
<213> ORGANISM: Artificial Sequence
<220> FEATURE:
<223> OTHER INFORMATION: synthetic oligomer

<400> SEQUENCE: 51
tctctgtttg acttagttgc tcg                                        23

<210> SEQ ID NO 52
<211> LENGTH: 62
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (30)..(62)
<223> OTHER INFORMATION: dT3/dA30 tail

<400> SEQUENCE: 52
ggttggctat acctaaagtc atgaatcctt ttaaaaaaaa aaaaaaaaaa aaaaaaaaaa    60
aa                                                               62

<210> SEQ ID NO 53
<211> LENGTH: 29
```

```
<212> TYPE: DNA
<213> ORGANISM: Artificial Sequence
<220> FEATURE:
<223> OTHER INFORMATION: synthetic oligomer

<400> SEQUENCE: 53
ggttggctat acctaaagtc atgaatcct                                          29

<210> SEQ ID NO 54
<211> LENGTH: 20
<212> TYPE: RNA
<213> ORGANISM: Artificial Sequence
<220> FEATURE:
<223> OTHER INFORMATION: synthetic oligomer

<400> SEQUENCE: 54
gucauggaca guuaucugac                                                    20

<210> SEQ ID NO 55
<211> LENGTH: 981
<212> TYPE: DNA
<213> ORGANISM: Erythrovirus B19

<400> SEQUENCE: 55
agtggtagcc gcgtcgtggg aggaagcttt ttacacgccg cttgcagatc agtttcgtga        60
actgttagta ggggttgact atgtatggga tggtgtaagg ggattacctg tttgctgtgt       120
ggaacatatt aataacagtg ggggagggtt ggggctttgt cctcattgta ttaatgtggg       180
agcttggtat aatggatgga aatttagaga gttactcca gacttagtgc gctgtagttg       240
tcatgtagga gcctctaacc catttctgt gttaacttgt aaaaaatgtg cttacctgtc       300
tggattacaa agctttgtag attatgagta aaaccactga caaatggtgg gaaagtagtg       360
acaaatttgc ccaggacgtg tataagcagt ttgtacaatt ttatgaaaaa gctactggaa       420
cagatttaga gcttattcaa atttttaaaag atcattacaa catttcttta gacaatcctt       480
tagaaaaccc ctcttcttta tttgacttag ttgctcgcat taaaagcaat cttaaaaact       540
ctccagacct atatagtcat catttttcaaa gccatggaca gttatctgac cacccccatg       600
ccttatcacc cagtaacagt agtacagaac ctagaggaga aaatgcagta ttatctagtg       660
aagacttaca caagcctggg caagttagca tacaattacc cggtactaac tatgttgggc       720
ctggcaatga gctacaagct gggcctccgc agaatgctgt ggacagtgct gcaaggattc       780
atgactttag gtatagccaa ttggctaagt tgggaataaa tccttatact cattggacgg       840
tagcagatga agaattgtta aaaaatataa aaatgaaac agggtttcaa gcacaagcag       900
taaaagacta ctttacttta aaaggtgcag ctgcccctgt ggcccatttt caaggaagtt       960
taccggaagt gcccgcgtac a                                                 981

<210> SEQ ID NO 56
<211> LENGTH: 53
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 56
aatttaatac gactcactat agggagacca acatagttag taccgggtag ttg              53
```

```
<210> SEQ ID NO 57
<211> LENGTH: 26
<212> TYPE: DNA
<213> ORGANISM: Artificial Sequence
<220> FEATURE:
<223> OTHER INFORMATION: synthetic oligomer

<400> SEQUENCE: 57
ccaacatagt tagtaccggg tagttg                                  26

<210> SEQ ID NO 58
<211> LENGTH: 61
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (28)..(39)
<223> OTHER INFORMATION: insert sequence

<400> SEQUENCE: 58
aatttaatac gactcactat agggagacct acgatgcatc caacatagtt agtaccgggt    60
a                                                             61

<210> SEQ ID NO 59
<211> LENGTH: 34
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(12)
<223> OTHER INFORMATION: insert or tag sequence

<400> SEQUENCE: 59
cctacgatgc atccaacata gttagtaccg ggta                         34

<210> SEQ ID NO 60
<211> LENGTH: 22
<212> TYPE: DNA
<213> ORGANISM: Artificial Sequence
<220> FEATURE:
<223> OTHER INFORMATION: synthetic oligomer

<400> SEQUENCE: 60
ccaacatagt tagtaccggg ta                                      22

<210> SEQ ID NO 61
<211> LENGTH: 49
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 61
aatttaatac gactcactat agggagacca acatagttag taccgggta         49
```

-continued

```
<210> SEQ ID NO 62
<211> LENGTH: 26
<212> TYPE: DNA
<213> ORGANISM: Artificial Sequence
<220> FEATURE:
<223> OTHER INFORMATION: synthetic oligomer

<400> SEQUENCE: 62
ccaacatagt tagtaccggg tarttg                                           26

<210> SEQ ID NO 63
<211> LENGTH: 65
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (28)..(39)
<223> OTHER INFORMATION: insert

<400> SEQUENCE: 63
aatttaatac gactcactat agggagacct acgatgcatc caacatagtt agtaccgggt      60
agttg                                                                 65

<210> SEQ ID NO 64
<211> LENGTH: 38
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(12)
<223> OTHER INFORMATION: insert or tag sequence

<400> SEQUENCE: 64
cctacgatgc atccaacata gttagtaccg ggtagttg                              38

<210> SEQ ID NO 65
<211> LENGTH: 38
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(12)
<223> OTHER INFORMATION: insert or tag sequence

<400> SEQUENCE: 65
cctacgatgc atccaacata gttagtaccg ggtarttg                              38

<210> SEQ ID NO 66
<211> LENGTH: 53
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 66
```
aatttaatac gactcactat agggagacca acatagttag taccgggtar ttg        53

<210> SEQ ID NO 67
<211> LENGTH: 65
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (28)..(39)
<223> OTHER INFORMATION: insert

<400> SEQUENCE: 67
aatttaatac gactcactat agggagacct acgatgcatc caacatagtt agtaccgggt        60 arttg        65

<210> SEQ ID NO 68
<211> LENGTH: 64
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (28)..(39)
<223> OTHER INFORMATION: insert

<400> SEQUENCE: 68
aatttaatac gactcactat agggagacct acgatgcata gtaccgggta gttgtacgct        60
aact        64

<210> SEQ ID NO 69
<211> LENGTH: 37
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(12)
<223> OTHER INFORMATION: insert or tag sequence

<400> SEQUENCE: 69
cctacgatgc atagtaccgg gtagttgtac gctaact        37

<210> SEQ ID NO 70
<211> LENGTH: 25
<212> TYPE: DNA
<213> ORGANISM: Artificial Sequence
<220> FEATURE:
<223> OTHER INFORMATION: synthetic oligomer

<400> SEQUENCE: 70
agtaccgggt arttgtaygc taact        25

<210> SEQ ID NO 71
<211> LENGTH: 37
<212> TYPE: DNA
<213> ORGANISM: Artificial Sequence

```
<220> FEATURE:
<223> OTHER INFORMATION: synthetic oligomer
<220> FEATURE:
<221> NAME/KEY: misc_feature
<222> LOCATION: (1)..(12)
<223> OTHER INFORMATION: insert or tag sequence

<400> SEQUENCE: 71
cctacgatgc atagtaccgg gtarttgtay gctaact                                37

<210> SEQ ID NO 72
<211> LENGTH: 52
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter

<400> SEQUENCE: 72
aatttaatac gactcactat agggagaagt accgggtart tgtaygctaa ct               52

<210> SEQ ID NO 73
<211> LENGTH: 65
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (28)..(39)
<223> OTHER INFORMATION: insert
<220> FEATURE:
<221> NAME/KEY: misc_feature
<222> LOCATION: (62)..(62)
<223> OTHER INFORMATION: n = a, c, t/u, g or other

<400> SEQUENCE: 73
aatttaatac gactcactat agggagacct acgatgcatc caacatagtt agtaccgggt       60 anttg                                                                  65

<210> SEQ ID NO 74
<211> LENGTH: 38
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(12)
<223> OTHER INFORMATION: insert or tag sequence
<220> FEATURE:
<221> NAME/KEY: misc_feature
<222> LOCATION: (35)..(35)
<223> OTHER INFORMATION: n = a, c, t/u, g or other

<400> SEQUENCE: 74
cctacgatgc atccaacata gttagtaccg ggtanttg                               38

<210> SEQ ID NO 75
<211> LENGTH: 26
<212> TYPE: DNA
<213> ORGANISM: Artificial Sequence
<220> FEATURE:
```

```
<223> OTHER INFORMATION: synthetic oligomer
<220> FEATURE:
<221> NAME/KEY: misc_feature
<222> LOCATION: (23)..(23)
<223> OTHER INFORMATION: n = a, c, t/u, g or other

<400> SEQUENCE: 75
ccaacatagt tagtaccggg tanttg                                          26

<210> SEQ ID NO 76
<211> LENGTH: 53
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (50)..(50)
<223> OTHER INFORMATION: n = a, c, t/u, g or other

<400> SEQUENCE: 76
aatttaatac gactcactat agggagacca acatagttag taccgggtan ttg            53

<210> SEQ ID NO 77
<211> LENGTH: 4517
<212> TYPE: DNA
<213> ORGANISM: Erythrovirus B19

<400> SEQUENCE: 77
catggtatat aagcagatga attttgtaaa actttctttc ctggctgctt tttactgggg     60
ataacttgct gttatttgcc tgctaattaa caggtattta tactaacttt taacttacta    120
acatggagct atttaggggt gtgttgcata tttcctctaa cattttagac tgcgctaatg    180
ataactggtg gtgctctatg ctagatttag atacttctga ctgggaacca ctaactcact    240
ctaacagact aatggcaata tatttaagta atgttgcttc taaactggat tttactgggg    300
ggccgctggc gggttgctta tactttttc  aggtggaatg taacaaattt gaggaaggct    360
accatattca tgtagttatt ggtggtccag gacttaatgc tagaaactta acagtgtgtg    420
tagaaggctt gttaataat  gttctttacc acctggtaaa tgaaagtgtt aagcttaaat    480
ttttgccagg aatgactact aagggaaagt atttagaga  tggagagcag tttatagaaa    540
attacctaat gaaaaaaatt cctttaaatg ttgtgtggtg tgtaactaat attgacgggt    600
atatagacac ctgtatttct gcatctttta gacgaggagc ttgccatgct aaaaaacctc    660
gaattagtgc aaaacagac  attgttaata atgaagcagg ggaatccagc tgtgtgagggg    720 gagatgtggt gccatttgct ggaaagggaa ccaaggcagg gttaaagttt caaacaatgg    780
taaattggtt atgtgaaaac agagtgttta ctgaagacaa atggaagtta gtggatttta    840
atcaatatac attgttaagc agtagtcata gtggagtttt caaatacaa  agtgcattaa    900 agctagctat ttataaggct actaacttag ttcctactag tacattttta atgcattcag    960
actttgagca ggttacctgc attaaagaaa ataaaatagt taaactatta ttatgccaaa   1020
attatgatcc tctttagtg  ggtcaacatg ttttaaagtg gattgacaaa aaatgtggta   1080
aaaaaaacac cctgtggttt tacgggcccc aagcactgg  aaaaacaaat ttggcaatgg   1140
ctattgccaa aactgtccca gtgtatgcca tggttaattg gaataatgaa attttccat    1200 ttaatgatgt agcggggaaa gtttggtgg  tctgggatga aggcattatt aagtccacta   1260
```

```
ttgtggaagc tgcaaaagcc attttaggtg ggcagccaac cagggtagat caaaaaatgc    1320
gtggcagtgt ggcagtgcct ggtgtgccag tggtaataac cagcaatggt gacattacct    1380
ttgttgtaag tggtaatacc actacaactg tccatgctaa agccttaaag gagcgcatgg    1440
taaagctaaa ctttaccgta agatgcagcc ctgacatggg cttacttaca gaggctgatg    1500
tacagcaatg gctaacttgg tgtaatgcac aaagctggaa ccactatgaa aactgggcaa    1560
taaactacac gtttgatttc cctggaataa atgcagatgc cctccaccca gacctccaaa    1620
ccgtccccat tgtcgcagac accagtgtca gcagcagtgg tggtgaaagc tctgaagaac    1680
tcagtgaaag cagctttttc aacctcatca ctccaggcgc ctggaacagt gaaacccccgc   1740 gctctagtac acccgtcccc gggaccagtt caggagaatc atttgtcgga agcccagttt    1800
cctccgaagt ggtagccgcg tcgtgggagg aagcctttta cactccactt gcagaccagt    1860
ttcgtgaact gttagttggg gttgactatg tgtgggatgg tgtaagggga ttgcctgttt    1920
gttgtgtgca gcatattaat aatagtgggg gagggttagg cctttgtcct tattgtatta    1980
atgtgggagc ttggtataat ggatggaagt ttcgagaatt tactccagat ttggtacggt    2040
gtagctgcca tgtaggagct tctaatccct tttctgtgtt aacctgcaaa aaatgtgctt    2100
acttgtctgg attacaaagt tttgtagatt atgagtaaaa aaagtggcaa atggtgggaa    2160
agtgatgata aatttgctaa ggacgtgtat aagcaatttg tagaatttta tgaaaaagtt    2220
actgggacag acttagagct tattcaaata ttaaaagatc attacaatat ttctttagat    2280
aatcccctag aaaacccatc ttccctgttt aacttagttg ctcgtattaa aagtaatctt    2340
aaagacactc cagacctata tagtcatcat tttcaaagtc atggacagtt atctgaccac    2400
ccccatgcct tatcacccgg tagcagtcat acagaaccta gaggagaaaa tgcagtatta    2460
tctagtgaag acttacacaa gcctgggcaa gttagcatac aactacccgg tactaactat    2520
gttgggcctg gcaatgagct acaagctggg ccccgcaaa gtgctgtgga cagtgctgca    2580
aggattcatg actttaggta tagccaattg gctaagctgg gaataaatcc atatactcat    2640
tggactgtag cagatgagga actgttaaaa aatataaaaa atgaaactgg gttcaagca    2700 caagcagtaa aagattactt tactttaaaa ggtgcagctg cccctgtggc ccattttcaa    2760
ggaagtttgc cggaagttcc cgcatacaac gcctcagaaa agtacccaag catgacttca    2820
gttaattctg cagaagccag cactggtgca ggagggggag gcagtaatcc tgtcaaaagc    2880
atgtggagtg aggggccac ttttactgcc aactctgtaa cttgtacatt ttccagacag    2940
tttttaattc catatgaccc agagcaccat tataaagtgt tttctcccgc agctagcagc    3000
tgccataatg ccagtgggaa agaggcaaag gtttgcacta ttagtcccat aatgggctac    3060
tcaacgccat ggagatactt agactttaat gctttaaact tatttttttc acctttagaa    3120
tttcaacatt taattgaaaa ttatggaagt atagcccctg aggctttaac tgttaccata    3180
tcagaaattg ctgttaaaga tgttacagac aaaacaggag gaggggtgca ggttactgac    3240
agtactacag ggcgtttatg tatgttagta gatcatgagt acaagtaccc atatgtgtta    3300
ggtcagggac aggataccct agccccagaa ctgcctattt gggtgtactt tccccctcaa    3360
tatgcttatt aacagtggg agatgtaaac acacaggaa tttcaggaga cagtaaaaaa    3420
ctagcaagtg aagaatcagc attttatgtt ttggaacaca gttcatttga actgttaggt    3480
acaggtggct ctgccactat gtcttataaa tttccaccag tgcccccaga aaacttggag    3540
ggttgtagcc agcactttta tgaaatgtac aaccccctgt atgggtcccg tttagggta    3600
```

-continued

```
cctgacacac tagggggaga ccctaaattt agatcattaa ctcacgaaga ccatgcaatt    3660
cagccacaaa actttatgcc tggcccacta gtaaactcag tgtccactaa agagggagac    3720
acttccaata caggcgccgg aaaagcccct acggggctta gtactggcac tagtcaaagc    3780
accagaatat ccctgcgccc aggaccagtg tctcagccat accatcactg ggacactgat    3840
aagtatgtca caggaataaa tgctatttca cacggacaaa ccacttatgg aaatgctgaa    3900
gacaaagagt atcagcaagg ggtaggaaga ttcccaaatg aaaaagagca acttaaacag    3960
ttacaaggcc taaacattca cacatacttt ccaaataaag gaacccaaca atacacagat    4020
caaattgaac gccccttaat ggtagggtct gtgtggaaca gaagagctct tcattatgaa    4080
agtcagctgt ggagtaaaat ccccaactta gatgacagtt ttaaaaccca atttgcagcc    4140
ctgggcgggt ggggtttaca tcaaccacct cctcaaatat ttttaaaaat attgccacaa    4200
agtggaccaa ttgggggtat taaatctatg ggaattacta ccttagttca atatgcagtg    4260
gggattatga cagttactat gacatttaaa ttgggacctc gtaaggctac tggtaggtgg    4320
aatccacagc ctggagtgta tcctcctcat gcagctggtc atttaccata tgtactatat    4380
gaccctacag ctacagatgc aaagcaacac cacagacacg gatatgaaaa gcctgaagaa    4440
ttgtggactg ccaaaagccg tgtgcaccca ttgtaaacac tccccaccgt gtcctcagcc    4500
aggaaccgta accaacc                                                  4517
```

```
<210> SEQ ID NO 78
<211> LENGTH: 64
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (28)..(39)
<223> OTHER INFORMATION: insert
<220> FEATURE:
<221> NAME/KEY: misc_feature
<222> LOCATION: (51)..(51)
<223> OTHER INFORMATION: n = a, c, t/u, g or other
<220> FEATURE:
<221> NAME/KEY: misc_feature
<222> LOCATION: (57)..(57)
<223> OTHER INFORMATION: n = a, c, t/u, g or other

<400> SEQUENCE: 78
aatttaatac gactcactat agggagacct acgatgcata gtaccgggta nttgtangct    60
aact                                                                64
```

```
<210> SEQ ID NO 79
<211> LENGTH: 37
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(12)
<223> OTHER INFORMATION: insert or tag sequence
<220> FEATURE:
<221> NAME/KEY: misc_feature
<222> LOCATION: (24)..(24)
<223> OTHER INFORMATION: n = a, c, t/u, g or other
<220> FEATURE:
<221> NAME/KEY: misc_feature
```

```
<222> LOCATION: (30)..(30)
<223> OTHER INFORMATION: n = a, c, t/u, g or other

<400> SEQUENCE: 79
cctacgatgc atagtaccgg gtanttgtan gctaact                             37

<210> SEQ ID NO 80
<211> LENGTH: 25
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (12)..(12)
<223> OTHER INFORMATION: n = a, c, t/u, g or other
<220> FEATURE:
<221> NAME/KEY: misc_feature
<222> LOCATION: (18)..(18)
<223> OTHER INFORMATION: n = a, c, t/u, g or other

<400> SEQUENCE: 80
agtaccgggt anttgtangc taact                                         25

<210> SEQ ID NO 81
<211> LENGTH: 52
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (39)..(39)
<223> OTHER INFORMATION: n = a, c, t/u, g or other
<220> FEATURE:
<221> NAME/KEY: misc_feature
<222> LOCATION: (45)..(45)
<223> OTHER INFORMATION: n = a, c, t/u, g or other

<400> SEQUENCE: 81
aatttaatac gactcactat agggagaagt accgggtant tgtangctaa ct           52

<210> SEQ ID NO 82
<211> LENGTH: 64
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (1)..(27)
<223> OTHER INFORMATION: promoter
<220> FEATURE:
<221> NAME/KEY: misc_feature
<222> LOCATION: (28)..(39)
<223> OTHER INFORMATION: insert

<400> SEQUENCE: 82
aatttaatac gactcactat agggagacct acgatgcata gtaccgggta rttgtaygct   60
aact                                                                64

<210> SEQ ID NO 83
<211> LENGTH: 11
<212> TYPE: DNA
<213> ORGANISM: Artificial Sequence
<220> FEATURE:
```

<223> OTHER INFORMATION: Synthetic Oligomer or residues 2428 to 2438 of
      SEQ ID NO:90

<400> SEQUENCE: 83
tacccggtac t                                                            11

<210> SEQ ID NO 84
<211> LENGTH: 15
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (4)..(4)
<223> OTHER INFORMATION: n is a, c, g, or t

<400> SEQUENCE: 84
caantacccg gtact                                                        15

<210> SEQ ID NO 85
<211> LENGTH: 36
<212> TYPE: DNA
<213> ORGANISM: Artificial Sequence
<220> FEATURE:
<223> OTHER INFORMATION: Synthetic Oligomer or residues 2414 to 2449 of
      SEQ ID NO:90

<400> SEQUENCE: 85
agttagcgta caactacccg gtactaacta tgttgg                                 36

<210> SEQ ID NO 86
<211> LENGTH: 39
<212> TYPE: DNA
<213> ORGANISM: Artificial Sequence
<220> FEATURE:
<223> OTHER INFORMATION: Synthetic Oligomer

<400> SEQUENCE: 86
gcagtattat ctagtgaaga cttacacaag cctgggcaa                              39

<210> SEQ ID NO 87
<211> LENGTH: 106
<212> TYPE: DNA
<213> ORGANISM: Artificial Sequence
<220> FEATURE:
<223> OTHER INFORMATION: Synthetic Oligomer

<400> SEQUENCE: 87
catggacagt tatctgacca cccccatgcc ttatcatcca gtaacagtca tgcagaacct       60
agaggagaaa atgcagtatt atctagtgaa gacttacaca agcctg                     106

<210> SEQ ID NO 88
<211> LENGTH: 146
<212> TYPE: DNA
<213> ORGANISM: Artificial Sequence
<220> FEATURE:
<223> OTHER INFORMATION: Synthetic Oligomer

<400> SEQUENCE: 88
catggacagt tatctgacca cccccatgcc ttatcatcca gtaacagtca tgcagaacct       60
agaggagaaa atgcagtatt atctagtgaa gacttacaca agcctgggca agttagcgta      120
caactacccg gtactaacta tgttgg                                           146

<210> SEQ ID NO 89
<211> LENGTH: 106
<212> TYPE: DNA
<213> ORGANISM: Artificial Sequence
<220> FEATURE:
<223> OTHER INFORMATION: Synthetic Oligomer

<400> SEQUENCE: 89

| | | |
|---|---|---|
| cttatcatcc agtaacagtc atgcagaacc tagaggagaa aatgcagtat tatctagtga | 60 |
| agacttacac aagcctgggc aagttagcgt acaactaccc ggtact | 106 |

<210> SEQ ID NO 90
<211> LENGTH: 4469
<212> TYPE: DNA
<213> ORGANISM: Erythrovirus B19

<400> SEQUENCE: 90

| | | |
|---|---|---|
| tgtgagctaa ctaacaggta tttatactac ttgttaacat actaacatgg agctatttac | 60 |
| aggggtgctt caagtttctt ctaatgttct ggactgtgct aacgataact ggaggagctc | 120 |
| tttactggat ttagacacct ctgactggga accactaact catactaaca gactaatggc | 180 |
| aatatactta agcagtgtgg cttctaagct tgactttacc gggggggccac tagcggggtg | 240 |
| cttgtacttt tttcaagtag aatgtaacac atttgaagaa ggctatcata ttcatgtggt | 300 |
| tattgggggg ccagggttaa accccagaaa cctaacagtg tgtgtagagg ggttatttaa | 360 |
| taatgtactt tatcaccttg taactggaaa tgtaaagcta aaattttgc caggaatgac | 420 |
| tacaaaaggc aaatacttta gagatggaga gcagtttata gaaaactatt taatgaaaaa | 480 |
| aataccttg aatgttgtat ggtgtgttac taatattgat ggatatatag atacctgtat | 540 |
| ttctgctact tttagaaggg gagcttgcca tgccaagaaa ccccgcatga ccacagccat | 600 |
| aaatgatact actagtgatg ctggagagtc tagcggcaca ggggcagagg ttgtgccatt | 660 |
| taatggaaaa ggaactaagg ctagcataaa gtttcaaact atggtaaact ggttgtgtga | 720 |
| aaatagagtg tttacagagg ataagtggaa accagttgac tttaaccagt acactttact | 780 |
| aagcagtagt cacagtggga gttttcaaat tcaaagtgca ctaaaactag caatttataa | 840 |
| agcaactaat ttagtgccta ctagcacatt tttattgcat acagactttg agcaggttat | 900 |
| gtgtattaaa gacaataaaa ttgttaaatt gttactttgt caaaactatg acccctatt | 960 |
| ggtggggcag catgtgttaa agtggattga taaaaatgt ggcaagaaaa atacactgtg | 1020 |
| gttttatggg ccgccaagta caggaaagac aaacttggca atggccattg ctaaaagtgt | 1080 |
| tccagtatat ggcatggtta actggaataa tgaaactttt ccatttaatg atgtagcagg | 1140 |
| gaaaagcttg gtggtctggg atgaaggtat tattaagtcc acaattgtag aagctgcaaa | 1200 |
| agccattta ggcgggcaac ctaccagggt agatcaaaaa atgcgtggaa gtgtagctgt | 1260 |
| gcctggagta cctgtggtta taaccagcaa tggtgacatt acttttgttg taagcgggaa | 1320 |
| cactacaaca actgtacatg ctaaagcctt aaaagagcgc atggtaaagt taaactttac | 1380 |
| tgtaagatgc agccctgaca tggggttact aacagaggct gatgtacaac agtggcttac | 1440 |
| atggtgtaat gcacaaagct gggaccacta tgaaaactgg gcaataaact acacttttga | 1500 |
| tttccctgga attaatgcag atgccctcca cccagacctc aaaccaccc caattgtcac | 1560 |
| agacaccagt atcagcagca gtggtggtga aagctctgaa gaactcagtg aaagcagctt | 1620 |
| ttttaacctc atcaccccag cgcgcctgaa cactgaaaacc ccgcgctcta gtacgcccat | 1680 |
| ccccgggacc agttcaggag aatcatttgt cggaagccca gtttcctccg aagttgtagc | 1740 |

```
tgcatcgtgg gaagaagcct tctacacacc tttggcagac cagtttcgtg aactgttagt    1800
tggggttgat tatgtgtggg acggtgtaag gggtttacct gtgtgttgtg tgcagcatat    1860
taacaatagt gggggaggct tgggactttg tccccattgc attaatgtag gggcttggta    1920
taatggatga aaatttcgag aatttacccc acatttggtg cggtgtagct gccatgtggg    1980
agcttctaat ccctttctg tgctaacctg caaaaaatgt gcttacctgt ctggattgca     2040
aagctttgta gattatgagt aaagaaagtg gcaatggtg ggaaagtgat gataaatttg     2100
ctaaagctgt gtatcagcaa ttagtggaat tttatgaaaa gcttactgga acagacttag    2160
agcttattca aatattaaaa gatcattaca atatttcttt agataatccc ctagaaaacc    2220
catcctctct gtttgactta gttactcgta ttaaaaataa ccttaaaaac tctccagact    2280
tacatagtca tcattttcaa agtcatggac agttatctga ccacccccat gccttatcat    2340
ccagtaacag tcatgcagaa cctagaggag aaaatgcagt attatctagt gaagacttac    2400
acaagcctgg gcaagttagc gtacaactac ccggtactaa ctatgttggg cctggcaatg    2460
agctacaaac tgggcccccg caaagtgctg ttgacagtgc tgcaaggatt catgacttta    2520
ggtatagcca actggctaag ttgggaataa atccatatac tcattggact gtagcagatg    2580
aagagctttt agaaaatata aaaaatgaaa ctgggtttca agcacaagta gtaaaagact    2640
actttacttt aaaaggtgca gctgcacctg tgcccatttt tcaaggaagt ttgccggaag    2700
ttcccgctta caacgcctca gaaaaatacc caagcatgac ttcagttaat tctgcagaag    2760
ccagcactgg tgcaggaggg gggggcagta atcctgtcaa aagcatgtgg agtgaggggg    2820
ccacttttag tgccaactct gtaacttgta cattttccag acagttttta attccatatg    2880
acccagagca ccattataag gtgttttctc ccgcagcaag cagctgccac aatgccagtg    2940
gaaaggaggc aaaggtttgc accattagtc ccataatggg atactcaacc ccatggagat    3000
atttagattt taatgcttta aatttgtttt tttcacctt agagtttcag catttaattg     3060
aaaactatgg aagtatagct cctgatgctt taactgtaac catatcagaa attgctgtta    3120
aggatgttac agacaaaact ggagggggga tacaagttac tgacagcact accgggcgcc    3180
tatgcatgtt agtagaccat gaatacaagt acccatatgt gttagggcaa ggtcaggata    3240
ctttagcccc agaacttcct atttgggtat actttccccc tcaatatgct tacttgacag    3300
taggagatgt taacacacaa ggaatctcta gagacagcaa aaaattagca agtgaagaat    3360
cagcatttta tgttttggaa cacagttctt ttcagctttt aggtacagga ggtacagcaa    3420
ctatgtctta taagtttcct ccagtgcccc cagaaaattt agagggctgc agtcaacact    3480
tttatgaaat gtacaatccc ttatacggat ctcgcttagg ggtccctgac acattaggag    3540
gtgacccaaa atttagatct ttaacacatg aagaccatgc aattcagccc caaaacttca    3600
tgccagggcc actagtaaac tcagtgtcta caaaggaggg agacagctct aatactggag    3660
ctggaaaagc cttaacaggc cttagcacag gcacctctca aaacactaga atatccttac    3720
gccctgggcc agtgtctcag ccatatcacc actgggacac agataaatat gtcacaggaa    3780
taaatgccat ttctcatggt cagaccacat atggtaatgc tgaagataaa gagtatcagc    3840
aaggagtggg tagatttcca aatgaaaaag aacagctaaa acagttacag ggtttaaaca    3900
tgcacaccta ttttcccaat aaaggaaccc agcaatatac agatcaaatt gagcgccccc    3960
taatggtggg ttctgtatgg aacagaagag cccttcacta tgaaagccag ctgtggagta    4020
aaattccaaa tttagatgac agttttaaaa ctcagtttgc agccttagga ggatgggggt    4080
tgcatcagcc acctcctcaa atatttttaa aaatattacc acaaagtggg cccattggag    4140
```

```
gtattaaatc aatgggaatt actaccttag ttcagtatgc cgtgggaatt atgacagtaa    4200
ctatgacatt taaattgggg ccccgtaaag ctacgggacg gtggaatcct caacctggag    4260
tatatccccc gcacgcagca ggtcatttac catatgtact atatgacccc acagctacag    4320
atgcaaaaca acaccacaga catggatatg aaaagcctga agaattgtgg acagccaaaa    4380
gccgtgtgca cccattgtaa acactcccca ccgtgccctc agccaggatg cgtaactaaa    4440 cgccccaccag taccacccag actgtacct                                     4469
```

<210> SEQ ID NO 91
<211> LENGTH: 172
<212> TYPE: DNA
<213> ORGANISM: Artificial Sequence
<220> FEATURE:
<223> OTHER INFORMATION: synthetic oligomer

<400> SEQUENCE: 91

```
agtcatggac agttatctga ccacccccat gccttatcat ccagtagcag tcatgcagaa     60
cctagaggag aaaatgcagt attatctagt gaagacttac acaagcctgg gcaagttagc    120
gtacaactac ccggtactaa ctatgttggg cctggcaatg agctacaagc tg            172
```

<210> SEQ ID NO 92
<211> LENGTH: 172
<212> TYPE: DNA
<213> ORGANISM: Artificial Sequence
<220> FEATURE:
<223> OTHER INFORMATION: synthetic oligomer

<400> SEQUENCE: 92

```
agtcatggac agttatctga ccacccccat gccttatcac ccagtagcag tcatacagaa     60
cctagaggag aaaatgcagt attatctagt gaagacttac acaagcctgg gcaagttagc    120
atacaactac ccggtactaa ctatgttggg cctggcaatg agctacaagc tg            172
```

<210> SEQ ID NO 93
<211> LENGTH: 172
<212> TYPE: DNA
<213> ORGANISM: Artificial Sequence
<220> FEATURE:
<223> OTHER INFORMATION: synthetic oligomer

<400> SEQUENCE: 93

```
agccatggac agttatctga ccacccccat gccttatcac ccagtaacag tagtacagaa     60
cctagaggag aaaatgcagt attatctagt gaagacttac acaagcctgg gcaagttagc    120
atacaattac ccggtactaa ctatgttggg cctggcaatg agctacaagc tg            172
```

<210> SEQ ID NO 94
<211> LENGTH: 12
<212> TYPE: DNA
<213> ORGANISM: Artificial Sequence
<220> FEATURE:
<223> OTHER INFORMATION: synthetic oligomer

<400> SEQUENCE: 94

```
cctacgatgc at                                                         12
```

<210> SEQ ID NO 95
<211> LENGTH: 20
<212> TYPE: DNA
<213> ORGANISM: Artificial Sequence
<220> FEATURE:

<223> OTHER INFORMATION: synthetic oligomer

<400> SEQUENCE: 95
gtcatatgcg acgatctcag                                              20

<210> SEQ ID NO 96
<211> LENGTH: 29
<212> TYPE: DNA
<213> ORGANISM: Artificial Sequence
<220> FEATURE:
<223> OTHER INFORMATION: Synthetic Oligomer or residues 2304 to 2332 of
      SEQ ID NO:90

<400> SEQUENCE: 96
catggacagt tatctgacca cccccatgc                                    29

<210> SEQ ID NO 97
<211> LENGTH: 22
<212> TYPE: DNA
<213> ORGANISM: Artificial Sequence
<220> FEATURE:
<223> OTHER INFORMATION: Synthetic Oligomer or residues 2428 to 2449 of
      SEQ ID NO:90

<400> SEQUENCE: 97
tacccggtac taactatgtt gg                                           22

<210> SEQ ID NO 98
<211> LENGTH: 77
<212> TYPE: DNA
<213> ORGANISM: Artificial Sequence
<220> FEATURE:
<223> OTHER INFORMATION: Synthetic Oligomer

<400> SEQUENCE: 98
cttatcatcc agtaacagtc atgcagaacc tagaggagaa aatgcagtat tatctagtga    60
agacttacac aagcctg                                                 77

<210> SEQ ID NO 99
<211> LENGTH: 63
<212> TYPE: DNA
<213> ORGANISM: Artificial Sequence
<220> FEATURE:
<223> OTHER INFORMATION: Synthetic Oligomer

<400> SEQUENCE: 99
gcagtattat ctagtgaaga cttacacaag cctgggcaag ttagcgtaca actacccggt    60
act                                                                63

<210> SEQ ID NO 100
<211> LENGTH: 131
<212> TYPE: DNA
<213> ORGANISM: Artificial Sequence
<220> FEATURE:
<223> OTHER INFORMATION: synthetic oligomer

<400> SEQUENCE: 100
gacagttatc tgaccacccc catgccttat catccagtaa cagtcatgca gaacctagag    60
gagaaaatgc agtattatct agtgaagact tacacaagcc tgggcaagtt agcgtacaac   120
tacccggtac t                                                      131

ASSAY FOR DETECTION OF HUMAN PARVOVIRUS NUCLEIC ACID

CROSS-REFERENCE TO RELATED APPLICATIONS

This application is a division of U.S. patent application Ser. No. 14/569,338, filed on Dec. 12, 2014, now allowed, which is a continuation of U.S. patent application Ser. No. 13/203,715, filed on Aug. 26, 2011, now issued as U.S. Pat. No. 8,921,039, which is a national phase entry under 35 U.S.C. § 371 of International Application No. PCT/US2010/025499, filed on Feb. 26, 2010, which claims the benefit of priority to U.S. Provisional Application No. 61/155,685, filed on Feb. 26, 2009, each of which is incorporated herein by reference in its entirety.

REFERENCE TO SEQUENCE LISTING

The instant application contains a Sequence Listing which has been submitted in ASCII format via EFS-Web and is hereby incorporated by reference in its entirety. Said ASCII Copy, created on Jun. 11, 2018, is named "Seq_Listing_gp234-pct_ST25" and is 38,019 bytes in size.

FIELD OF THE INVENTION

This invention relates to diagnostic methods and compositions for detecting a human infectious agent, and specifically relates to methods and compositions for detecting in vitro the nucleic acid of human parvovirus genotypes 1, 2 and 3.

BACKGROUND OF THE INVENTION

Human parvovirus (genus *Erythrovirus*) is a blood borne, non-enveloped virus that has a single-stranded DNA (ssDNA) genome of about 5.5 kb (Shade et al., 1986, *J. Virol.* 58(3): 921-936, Brown et al., 1997, *Ann. Rev. Med.* 48: 59-67). Individual virions contain one copy of either the plus or minus strand of the genome, represented in approximately equal numbers. The ssDNA genome has inverted terminal repeats that form 5' and 3' hairpins of about 350 nt, which are essential for viral replication. The genome includes two open reading frames on the plus strand, which code for structural proteins (VP1 and VP2) and non-structural protein (NS1).

At one time it was believed that human parvovirus was highly conserved at less than 2% genetic diversity. More recently, though, it has been discovered that a human *Erythrovirus* isolate, originally termed V9, has a greater than 11% divergence in genome sequence compared to B19, with the most striking DNA dissimilarity is >20%, observed within the p6 promoter region. The V9 isolate was determined to have a clinical presence of greater than 11%, as well. Now the human *Erythrovirus* group is divided into three distinct virus genotypes: genotype 1 (B19), genotype 2 (A6- and LaLi-like), and genotype 3 (V9-like). (Servant et al., 2002, *J. Virol.* 76(18): 9124-34; Ekman et al., 2007, *J. Virol.* 81(13): 6927-35). Servant et al., refer to genotype 1 as viruses corresponding to parvovirus B19 and refer to genotypes 2 and 3 as viruses corresponding to parvovirus V9-related. Ekman et al., refer to genotypes 1-3 as all corresponding to parvovirus B19. For convenience herein, genotypes 1, 2 and 3 are referred to as parvovirus genotypes 1, 2 and 3 or human parvovirus genotypes 1, 2 and 3.

Current nucleic acid detection assays do not accurately detect all parvovirus genotypes. As a result of these deficient assays, many plasma pools remain contaminated with human parvovirus. Similarly, many cases of parvovirus infection are not properly diagnosed. Thus, there is a need for a nucleic acid test that detects human parvovirus genotypes 1, 2 and 3.

Infection with human parvovirus can occur via respiratory transmission or through infected blood or blood products. Viremia reaches high levels at about a week after inoculation, and is generally cleared within about two weeks following infection. Infected individuals may exhibit no symptoms, or have erythema infectiosum symptoms that include mild flu-like symptoms, rash, and/or temporary arthritis-like joint pain (arthropathy). Children are more likely than adults to develop the rash (called "fifth disease"), whereas arthropathy is a common symptom in adults. More serious problems occur in susceptible patients, including aplastic crisis in patients with hemolytic anemias, and persistent parvovirus infection and other hematologic changes in immunosuppressed patients. In women, human parvovirus infections have been associated with loss of about 10% of early pregnancies due to fetal death. Thus, the failure to detect parvovirus in a pooled plasma sample or for diagnosis of infection has serious consequences.

Parvovirus is a relatively resistant to viral inactivation, e.g., by chemical or heat-treatment methods used to destroy infective particles in blood, serum or plasma. Also, high viral concentrations in a sample may overwhelm viral depletion methods used to remove viral contaminants from the sample. Parvovirus in blood, plasma or plasma-derived products can infect additional individuals who receive contaminated transfusions or products. Plasma derivatives are often made from pooled donations (e.g., a pool of thousands of individual donations) resulting in the risk that a single contaminated donation could contaminate the pool and products derived from it. Thus, there is a need to detect the presence of human parvovirus types 1, 2 and 3 in biological samples, such as donated blood or plasma to prevent further infection. Further, there is a need that detection assays provide a detection sensitivity that allows for detection of low titers of virus, as may occur early in an infection or in diluted or pooled samples. Parvovirus nucleic acid detection assays that can detect an appropriate level of contamination may facilitate removal of infected donated units from the blood supply or contaminated lots of pooled plasma before use.

Many immunodiagnostic methods detect anti-parvovirus antibodies (IgM or IgG) present in an individual's serum or plasma (e.g., see PCT Nos. WO 96/09391 by Wolf et al. and WO 96/27799 by Hedman et al.). These methods have limitations in detecting recent or current infections because they rely on detecting the body's response to the infectious agent. The rapid rise in viremia following infection results in high levels of parvovirus in an individual's blood without corresponding detectable levels of anti-parvovirus antibodies (See, e.g., U.S. Pat. No. 7,094,541 to Bentano et al at Example 4). Thus, immunological-based detection assays are susceptible to false negative results. Furthermore, viremia is often quickly cleared, yet a person may remain antibody-positive in the absence of these infective particles, thusly leading to false positive results. As many as 90% of adults are seropositive for parvovirus, making accurate immunological detection of recent or current infections difficult. Other similar assays detect the presence of parvovirus by detecting the virus or empty viral capsid bound to a purified cellular receptor (U.S. Pat. No. 5,449,608 to Young et al.), and these immuno-based assays experience similar problems.

DNA hybridization and amplification methods have also been used to detect human parvovirus, though these tests are generally directed to the detection of genotype 1 only. Yet, U.S. and European regulatory bodies have promulgated standards specifying that plasma pools used for manufacturing anti-D immunoglobulin and other plasma derivatives can contain no more than 10,000 IU/ml (10 IU/microliter in Europe) of any human parvovirus. As discussed above, therapeutic plasma pools and diagnostic tests need similarly to reliably identify human parvovirus types 1, 2 and 3. Thus, there is a need in the art for compositions, kits and methods useful in the in vitro nucleic acid detection of human parvovirus types 1, 2 and 3.

SUMMARY OF THE INVENTION

The present invention relates to compositions, kits and methods for the detection of human parvovirus genotypes 1, 2 and 3. These compositions, kits and methods are configured to amplify target sequences of human parvovirus nucleic acids and are configured to detect target sequences of human parvovirus nucleic acids or amplified nucleic acids. In certain embodiments and aspects, particular regions within target sequences of the human parvovirus have been identified as preferred targets for nucleic acid amplification reactions of a sample, including biological specimens derived from infected humans Amplification oligomers or detection oligomers targeting these regions may share common core sequences, and thus provide a plurality of particularly preferred amplification oligomers or detection oligomers Amplification products generated using such particularly preferred amplification oligomers will contain target specific sequences useful for specific detection of human parvovirus from a sample. Detection of an amplification product can include any of a variety of methods, including, but not limited to, probe-based detection, hybridization protection assays, molecular torch, molecular beacon or molecular switch based assays, mass spectrometry, MALDI-TOF mass spectrometry, ESI-TOF mass spectrometry, real-time detection assays, gel-electrophoresis, SDS-PAGE electrophoresis and the like. These preferred regions of a target sequence provide improvements in relation to specificity, sensitivity, or speed of detection of genotype 1, as well as the ability to quickly and specifically detect genotypes 2 and 3 with high sensitivity. Using these amplification and/or detection oligomers, the methods include the steps of amplifying target sequences within human parvovirus genome and detecting the amplification products. Detection oligomers are preferably used for detecting amplified products.

In describing the preferred regions within a target sequence of a human parvovirus nucleic acid, reference is made to GenBank Accession No. DQ225149.1 gi:77994407, entered at GenBank on Oct. 26, 2005 with non-sequence related updates on Sep. 12, 2006. This accession number is provided in the sequence listing as SEQ ID NO:90. When discussing regions within a target sequence, the regions are referred to as corresponding to certain residues of SEQ ID NO:90. Such regions are given their own SEQ ID NOS and are provided in the sequence listing. Similarly, amplification oligomer combinations are sometimes referred to as being configured to generate from SEQ ID NO:90 amplicons containing target specific sequences, which are portions of the target sequence. One of ordinary skill in the art will understand that these references to SEQ ID NO:90 are provided for convenience in describing the current compositions, kits and methods. The ordinarily skilled artisan understands that such a reference for convenience does not limit the current compositions, kits and methods to use only with SEQ ID NO:90, but rather these compositions, kits and methods are broadly useful for the amplification and/or detection of human parvovirus genotypes 1, 2 or 3.

An embodiment provides an amplification oligomer combination comprising at least one primer oligomer member and at least one promoter-based oligomer member comprising a target binding sequence from 10-40 nucleobases in length and configured to specifically hybridize to all or a portion of a region of a target sequence of a human parvovirus nucleic acid, said region corresponding to residue 2428 to residue 2438 of GenBank Accession No. DQ225149.1 gi:77994407 (SEQ ID NO:83); wherein this amplification oligomer combination is configured to generate from GenBank Accession No. DQ225149.1 gi:77994407 an amplicon that is about 100 nucleobases in length to about 225 nucleobases in length and comprises a target specific sequence that that contains SEQ ID NO:39. In one aspect of this embodiment, the amplicon further comprises a non-target specific sequence selected from the group consisting of a tag sequence, an insert sequence, a promoter sequence that is SEQ ID NO:19, SEQ ID NO:94, SEQ ID NO:95 and combinations thereof.

In one aspect of this embodiment, the amplification oligomer combination is configured to generate from GenBank Accession No. DQ225149.1 gi:77994407 an amplicon that is about 100 nucleobases in length to about 225 nucleobases in length and comprises a target specific sequence that that contains SEQ ID NO:99. In another aspect of this embodiment, the amplification oligomer combination is configured to generate an amplicon comprising a target specific sequence that contains SEQ ID NO:86. In another aspect of this embodiment, the amplification oligomer combination is configured to generate an amplicon comprising a target specific sequence that contains SEQ ID NO:87. In another aspect of this embodiment, the amplification oligomer combination is configured to generate an amplicon comprising a target specific sequence that contains SEQ ID NO:100. In another aspect of this embodiment, the amplification oligomer combination is configured to generate an amplicon comprising a target specific sequence that contains SEQ ID NO:25. In another aspect of this embodiment, the amplification oligomer combination is configured to generate an amplicon comprising a target specific sequence that contains SEQ ID NO:88. In another aspect of this embodiment, the amplification oligomer combination is configured to generate an amplicon comprising a target specific sequence that contains SEQ ID NO:89. In another aspect of this embodiment, the amplification oligomer combination is configured to generate an amplicon comprising a target specific sequence that contains SEQ ID NO:26. In another aspect of this embodiment, the amplification oligomer combination is configured to generate an amplicon comprising a target specific sequence that contains SEQ ID NO:98. In another aspect of this embodiment, the amplification oligomer combination is configured to generate an amplicon comprising a target specific sequence that is 90% identical to SEQ ID NO:88. In another aspect of this embodiment, the amplification oligomer combination is configured to generate an amplicon comprising a target specific sequence that is 95% identical to SEQ ID NO:88. In another aspect of this embodiment, the amplification oligomer combination is configured to generate an amplicon comprising a target specific sequence that is 90% identical to SEQ ID NO:88 and that contains SEQ ID NO:96.

In a further aspect of this embodiment, the at least one primer oligomer member comprises a target binding sequence configured to specifically hybridize to all or a portion of a region of a target sequence of a human parvovirus nucleic acid said region corresponding to residues 2304 to 2332 of GenBank Accession No. DQ225149.1 gi:77994407 (SEQ ID NO:96). In another aspect of this embodiment, the at least one primer oligomer member comprises a target binding sequence configured to specifically hybridize to all or a portion of a region of a target sequence of a human parvovirus nucleic acid said region corresponding to residues 2302 to 2319 of GenBank Accession No. DQ225149.1 gi:77994407 (SEQ ID NO:38). In another aspect of this embodiment, the at least one primer oligomer member comprises a target binding sequence configured to specifically hybridize to all or a portion of a region of a target sequence of a human parvovirus nucleic acid said region corresponding to residues 2298 to 2332 of GenBank Accession No. DQ225149.1 gi:77994407 (SEQ ID NO:35). In another aspect of this embodiment, the at least one primer oligomer member further comprises a 5' tag sequence. In another aspect of this embodiment, the at least one primer member is selected from the group consisting of SEQ ID NO:18, SEQ ID NO:47, SEQ ID NO:48, SEQ ID NO:49, SEQ ID NO:50 and combinations thereof. In a particular aspect of this embodiment, the at least one primer member is SEQ ID NO:50. In a particular aspect of this embodiment, the at least one primer member is SEQ ID NO:47.

In a further aspect of this embodiment, the amplification oligomer combination comprises at least one primer oligomer member comprising a target binding sequence configured to specifically hybridize to all or a portion of a region of a target sequence of a human parvovirus nucleic acid said region corresponding to residues 2308 to 2332 of GenBank Accession No. DQ225149.1 gi:77994407 (SEQ ID NO:96), and wherein said amplification oligomer combination is configured to generate an amplicon that comprises a target specific sequence that contains SEQ ID NO:99. In another aspect of this embodiment, said primer member is selected from the group consisting of SEQ ID NOS:18, 47, 48, 49 and 50. In another aspect of this embodiment, said primer oligomer member is SEQ ID NO:50. In another aspect of this embodiment, said primer oligomer member is SEQ ID NO:47. In another aspect of this embodiment, said promoter-based oligomer member comprises a target binding sequence containing SEQ ID NO:84. In another aspect of this embodiment, said promoter-based oligomer member is configured to specifically hybridize with all or a portion of a region within a target sequence of a human parvovirus nucleic acid, said region corresponding to residues 2414 to 2449 of GenBank Accession No. DQ225149.1 gi:77994407 (SEQ ID NO:85).

In a further aspect of this embodiment, the at least one promoter-based oligomer member is configured to specifically hybridize with all or a portion of a region of a target sequence of a human parvovirus nucleic acid, said region corresponding to SEQ ID NO:85. In another aspect of this embodiment, the at least one promoter based oligomer member comprises a target binding sequence containing SEQ ID NO:84. In another aspect of this embodiment, the at least one promoter-based oligomer member comprises a target binding sequence selected from the group consisting of SEQ ID NO:24, SEQ ID NO:57; SEQ ID NO:60, SEQ ID NO:62, SEQ ID NO:70, SEQ ID NO:75, SEQ ID NO:80 and combinations thereof. In a particular aspect of this embodiment, the at least one promoter-based oligomer member comprises a target binding sequence that is SEQ ID NO:75. In a particular aspect of this embodiment, the at least one promoter-based oligomer member comprises a target binding sequence that is SEQ ID NO:80. In a particular aspect of this embodiment, the at least one promoter based oligomer member is a first promoter-based oligomer member comprising a target binding sequence that is SEQ ID NO:75 and a second promoter-based oligomer member comprising a target binding sequence that is SEQ ID NO:80. In another aspect of this embodiment, the at least one promoter-based oligomer member is selected from the group consisting of SEQ ID NO:23, SEQ ID NO:56, SEQ ID NO:61. SEQ ID NO:66, SEQ ID NO:72, SEQ ID NO:76, SEQ ID NO:81 and combinations thereof. In a particular aspect of this embodiment, the at least one promoter-based oligomer member is SEQ ID NO:76. In a particular aspect of this embodiment, the at least one promoter-based oligomer member comprises a target binding sequence that is SEQ ID NO:81. In a particular aspect of this embodiment, the at least one promoter based oligomer member is a first promoter-based oligomer member comprising a target binding sequence that is SEQ ID NO:76 and a second promoter-based oligomer member comprising a target binding sequence that is SEQ ID NO:81. In a further aspect of this embodiment, the at least one promoter-based oligomer member further comprises an internal tag sequence. In another aspect of this embodiment, the at least one promoter based oligomer is selected from the group consisting of SEQ ID NOS:58, 63, 67, 68, 73, 78, 82 and combinations thereof. In a particular aspect of this embodiment, the at least one promoter based oligomer is SEQ ID NO:73. In a particular aspect of this embodiment, the at least one promoter based oligomer is SEQ ID NO:78. In a particular aspect of this embodiment, the at least one promoter based oligomer member is a first promoter-based oligomer member comprising a target binding sequence that is SEQ ID NO:73 and a second promoter-based oligomer member comprising a target binding sequence that is SEQ ID NO:78.

In a further aspect of this embodiment, the at least one primer oligomer member is SEQ ID NO:50 and the at least one promoter-based oligomer member is selected from the group comprising SEQ ID NOS:73, 75, 76, 78, 80, 81 and combinations thereof. In a particular aspect of this embodiment, the at least one primer oligomer member is SEQ ID NO:50 and the at least one promoter-based oligomer member is SEQ ID NOS:73 and 78. In another aspect of this embodiment, the at least one primer oligomer member is SEQ ID NO:47 and the at least one promoter-based oligomer member is selected from the group comprising SEQ ID NOS:73, 75, 76, 78, 80, 81 and combinations thereof. In a particular aspect of this embodiment, the at least one primer oligomer member is SEQ ID NO:47 and the at least one promoter-based oligomer member is SEQ ID NOS:73 and 78.

In a further aspect of this embodiment there is provided at least one primer oligomer member comprising a target binding sequence configured to specifically hybridize to all or a portion of a region of a target sequence of a human parvovirus nucleic acid, wherein said region corresponds to residues 2304-2332 of GenBank Accession No. DQ225149.1 gi:77994407 (SEQ ID NO:96), and wherein said amplification oligomer combination is configured to generate from GenBank Accession No. DQ225149.1 gi:77994407 and amplicon comprising a target specific sequence that contains SEQ ID NO:99. In another aspect, the primer oligomer member is selected from the group consisting of SEQ ID NOS:18, 47, 48, 49 and 50. In another aspect, the primer oligomer member is SEQ ID NO:50. In another aspect, the primer oligomer member is SEQ ID NO:47. In another aspect, the amplification oligomer combination comprises promoter-based oligomer member comprising a target binding sequence containing SEQ ID NO:84. In another aspect, the amplification oligomer combination comprises promoter-based oligomer member configured to specifically hybridize with all or a portion of a region within a human parvovirus nucleic acid, said region corresponding to SEQ ID NO:85.

In another embodiment there is provided a method for the detection of human parvovirus from a sample comprising the steps of: obtaining a sample suspected of containing human parvovirus type 1, type 2, or type 3; contacting said sample with an amplification oligomer combination; wherein the amplification oligomer combination comprises at least one primer oligomer member and at least one promoter-based oligomer member comprising a target binding sequence from 10-40 nucleobases in length and configured to specifically hybridize to a region of a target nucleic acid of a human parvovirus, said region corresponding to residues 2428 to 2438 of GenBank Accession No. DQ225149.1 gi:77994407 (SEQ ID NO:83); wherein this amplification oligomer combination is configured to generate from said GenBank Accession No. DQ225149.1 gi:77994407 an amplicon that is about 100 nucleobases in length to about 225 nucleobases in length and that comprises a target specific sequence that contains SEQ ID NO:39; performing an amplification reaction on said sample to generate an amplicon from a human parvovirus in said sample; and detecting said amplicon; wherein the presence of an amplicon as determined by said detecting step indicates that one or more of human parvovirus genotypes types 1, 2 or 3 are present in said sample.

In one aspect of this embodiment, the amplification oligomer combination is configured to generate an amplicon comprising a target specific sequence containing SEQ ID NO:99. In another aspect of this embodiment, the amplification oligomer combination is configured to generate an amplicon containing SEQ ID NO:86. In another aspect of this embodiment, the amplification oligomer combination is configured to generate an amplicon containing SEQ ID NO:87. In another aspect of this embodiment, the amplification oligomer combination is configured to generate an amplicon containing SEQ ID NO:100. In another aspect of this embodiment, the amplification oligomer combination is configured to generate an amplicon containing SEQ ID NO:25. In another aspect of this embodiment, the amplification oligomer combination is configured to generate an amplicon containing SEQ ID NO:88. In another aspect of this embodiment, the amplification oligomer combination is configured to generate an amplicon containing SEQ ID NO:89. In another aspect of this embodiment, the amplification oligomer combination is configured to generate an amplicon comprising a target specific sequence containing SEQ ID NO:26. In another aspect of this embodiment, the amplification oligomer combination is configured to generate an amplicon containing SEQ ID NO:98. In another aspect of this embodiment, the amplification oligomer combination is configured to generate an amplicon comprising a target specific sequence that is 90% identical to SEQ ID NO:88. In another aspect of this embodiment, the amplification oligomer combination is configured to generate an amplicon comprising a target specific sequence that is 95% identical to SEQ ID NO:88. In another aspect of this embodiment, the amplification oligomer combination is configured to generate an amplicon comprising a target specific sequence that is 90% identical to SEQ ID NO:88 and that contains SEQ ID NO:96.

In a further aspect of this embodiment, the at least one primer oligomer member comprises a target binding sequence configured to specifically hybridize to all or a portion of a region within a target sequence of a human parvovirus nucleic acid, wherein said region corresponds to residues 2304 to 2332 of GenBank Accession No. DQ225149.1 gi:77994407 (SEQ ID NO:96). In another aspect of this embodiment, the at least one primer oligomer member further comprises a 5' tag sequence. In another aspect of this embodiment, the at least one primer member is selected from the group consisting of SEQ ID NO:18, SEQ ID NO:47, SEQ ID NO:48, SEQ ID NO:49, SEQ ID NO:50 and combinations thereof. In a particular aspect of this embodiment, the at least one primer member is SEQ ID NO:50. In a particular aspect of this embodiment, the at least one primer member is SEQ ID NO:47.

In a further aspect of this embodiment, the at least one promoter-based oligomer member is configured to specifically hybridize with all or a portion of a region within a target sequence of a human parvovirus nucleic acid, said region corresponding to residue 2414 to residue 2449 of GenBank Accession No. DQ225149.1 gi:77994407 (SEQ ID NO:85). In another aspect of this embodiment, the at least one promoter-based oligomer member comprises a target binding sequence containing SEQ ID NO:84. In another aspect of this embodiment, the at least one promoter-based oligomer member is configured to specifically hybridize with all or a portion of a region within a target sequence of a human parvovirus nucleic acid, said region corresponding to residue 2428 to residue 2449 of said GenBank Accession No. DQ225149.1 gi:77994407 (SEQ ID NO:97). In another aspect of this embodiment, the at least one promoter-based oligomer member comprises a target binding sequence selected from the group consisting of SEQ ID NO:24, SEQ ID NO:57; SEQ ID NO:60, SEQ ID NO:62, SEQ ID NO:70, SEQ ID NO:75, SEQ ID NO:80 and combinations thereof. In a particular aspect of this embodiment, the at least one promoter-based oligomer member comprises a target binding sequence that is SEQ ID NO:75. In a particular aspect of this embodiment, the at least one promoter-based oligomer member comprises a target binding sequence that is SEQ ID NO:80. In a particular aspect of this embodiment, the at least one promoter based oligomer member is a first promoter-based oligomer member comprising a target binding sequence that is SEQ ID NO:75 and a second promoter-based oligomer member comprising a target binding sequence that is SEQ ID NO:80. In another aspect of this embodiment, the at least one promoter-based oligomer member is selected from the group consisting of SEQ ID NO:23, SEQ ID NO:56, SEQ ID NO:61. SEQ ID NO:66, SEQ ID NO:72, SEQ ID NO:76 and combinations thereof. In a particular aspect of this embodiment, the at least one promoter-based oligomer member is SEQ ID NO:76. In a particular aspect of this embodiment, the at least one promoter-based oligomer member comprises a target binding sequence that is SEQ ID NO:81. In a particular aspect of this embodiment, the at least one promoter based oligomer member is a first promoter-based oligomer member comprising a target binding sequence that is SEQ ID NO:76 and a second promoter-based oligomer member comprising a target binding sequence that is SEQ ID NO:81. In a further aspect of this embodiment, the at least one promoter-based oligomer member further comprises an internal tag sequence. In another aspect of this embodiment, the at least one promoter based oligomer is selected from the group consisting of SEQ ID NOS:58, 63, 67, 68, 73, 78 and combinations thereof. In a particular aspect of this embodiment, the at least one promoter based oligomer is SEQ ID NO:73. In a particular aspect of this embodiment, the at least one promoter based oligomer is SEQ ID NO:78. In a particular aspect of this embodiment, the at least one promoter based oligomer member is a first promoter-based oligomer member comprising a target binding sequence that is SEQ ID NO:73 and a second promoter-based oligomer member comprising a target binding sequence that is SEQ ID NO:78.

In a further aspect of this embodiment, the at least one primer oligomer member is SEQ ID NO:50 and the at least one promoter-based oligomer member is selected from the group comprising SEQ ID NOS:73, 75, 76, 78, 80, 81 and combinations thereof. In a particular aspect of this embodiment, the at least one primer oligomer member is SEQ ID NO:50 and the at least one promoter-based oligomer member is SEQ ID NOS:73 and 78. In another aspect of this embodiment, the at least one primer oligomer member is SEQ ID NO:47 and the at least one promoter-based oligomer member is selected from the group comprising SEQ ID NOS:73, 75, 76, 78, 80, 81 and combinations thereof. In a particular aspect of this embodiment, the at least one primer oligomer member is SEQ ID NO:47 and the at least one promoter-based oligomer member is SEQ ID NOS:73 and 78.

In a further aspect of this embodiment there is provided at least one primer oligomer member comprising a target binding sequence configured to specifically hybridize to all or a portion of a region of a target sequence of a human parvovirus nucleic acid, wherein said region corresponds to residues 2304-2332 of GenBank Accession No. DQ225149.1 gi:77994407 (SEQ ID NO:96), and wherein said amplification oligomer combination is configured to generate from GenBank Accession No. DQ225149.1 gi:77994407 and amplicon comprising a target specific sequence that contains SEQ ID NO:99. In another aspect, the primer oligomer member is selected from the group consisting of SEQ ID NOS:18, 47, 48, 49 and 50. In another aspect, the primer oligomer member is SEQ ID NO:50. In another aspect, the primer oligomer member is SEQ ID NO:47. In another aspect, the amplification oligomer combination comprises promoter-based oligomer member comprising a target binding sequence containing SEQ ID NO:84. In another aspect, the amplification oligomer combination comprises promoter-based oligomer member configured to specifically hybridize with all or a portion of a region within a target sequence of human parvovirus nucleic acid, said region corresponding to SEQ ID NO:85.

In a further aspect of this embodiment, the detecting step is a hybridization protection assay that utilizes a detection probe that is 15 to 40 nucleobases in length and comprises a target binding sequence configured to specifically hybridize to all or a portion of a region within a target sequence of human parvovirus amplified nucleic acid, said region corresponding to residues 2376 to 2409 of GenBank Accession No. DQ225149.1 gi:77994407 (SEQ ID NO:33). In another aspect of this embodiment, detection probe comprises a target binding sequence configured to specifically hybridize to all or a portion of a region within a target sequence of human parvovirus amplified nucleic acid, said region corresponding to residues 2379 to 2396 of GenBank Accession No. DQ225149.1 gi:77994407 (SEQ ID NO:40). In another aspect of this embodiment, the detection probe comprises a target binding sequence that contains 5'-GTGAAGAC-3'. In another aspect of this embodiment, the detection probe is substantially similar to a detection probe selected from the group consisting of: SEQ ID NOS:28, 30, 31, 32, 42, 43, 44 and 46. In a particular aspect of this embodiment, the detection probe is SEQ ID NO:42.

In a particular aspect of this embodiment, the at least one primer oligomer member is SEQ ID NO:47, and the at least one promoter-based oligomer member is SEQ ID NOS:73 and 78, and the detecting step is a hybridization protection assay that utilizes a detection probe that is SEQ ID NO:42. In a particular aspect of this embodiment, the at least one primer oligomer member that is SEQ ID NO:50 and the at least one promoter-based oligomer member is SEQ ID NOS:73 and 78, and the detecting step is a hybridization protection assay that utilizes a detection probe that is SEQ ID NO:42.

It should be understood that both the foregoing general description and the following detailed description are exemplary only and are not restrictive of the invention. The detailed description and examples illustrate various embodiments and explain the principles of the invention.

DETAILED DESCRIPTION OF THE INVENTION

This application discloses oligonucleotide sequences configured for use as amplification oligomers and detection probe oligomers for detecting by an in vitro nucleic acid amplification assay parvovirus types 1, 2 and 3 nucleic acid sequences present in a biological sample. An embodiment of the method uses transcription-mediated nucleic acid amplification (as previously disclosed in detail in U.S. Pat. Nos. 5,399,491 and 5,554,516 to Kacian et al.). Methods for detecting amplified nucleic acid use sequence-specific probes that hybridize specifically to a portion of the amplified sequences. In one aspect, the method uses any known homogeneous detection step to detect, in a mixture, a labeled probe that is bound to an amplified nucleic acid (e.g., as disclosed by Arnold et al., Clin. Chem. 35:1588-1594 (1989); U.S. Pat. No. 5,658,737 to Nelson et al., and 5,118,801 and 5,312,728 to Lizardi et al.). This application also discloses oligonucleotide sequences that are useful for capturing parvovirus types 1, 2 and 3 target DNA by using nucleic acid hybridization techniques. One embodiment of the capturing step uses magnetic particles to separate the captured target (see U.S. Pat. No. 6,110,678 to Weisburg et al.).

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

By "biological sample" is meant any tissue or material derived from a living or dead human which may contain parvovirus nucleic acid, including, for example, sputum, peripheral blood, plasma, serum, biopsy tissue including lymph nodes, respiratory tissue or exudates, or other body fluids, tissues or materials. The sample may be treated to physically, chemically and/or mechanically disrupt tissue or cell structure, thus releasing intracellular components. Sample preparation may use a solution that contains buffers, salts, detergents and the like which are used to prepare the sample for analysis.

By "nucleic acid" is meant a multimeric compound comprising two or more covalently bonded nucleosides or nucleoside analogs which have nitrogenous heterocyclic bases, or base analogs, linked together by nucleic acid backbone linkages (e.g., phosphodiester bonds) to form a polynucleotide. Conventional RNA and DNA are included in the term "nucleic acid" as are analogs thereof. The nucleic acid backbone may include a variety of linkages, for example, one or more of sugar-phosphodiester linkages, peptide-nucleic acid bonds (see PCT No. WO 95/32305 by Hydig-Hielsen et al.), phosphorothioate or methylphosphonate linkages or mixtures of such linkages in a single oligonucleotide. Sugar moieties in the nucleic acid may be either ribose or deoxyribose, or similar compounds with known substitutions, such as, for example, 2' methoxy substitutions and 2' halide substitutions (e.g., 2'-F). Conventional nitrogenous bases (A, G, C, T, U), known base analogs (e.g., inosine; see *The Biochemistry of the Nucleic Acids* 5-36, Adams et al., ed., 11$^{th}$ ed., 1992), derivatives of purine or pyrimidine bases (e.g., N$^4$-methyl deoxygaunosine, deaza- or aza-purines and deaza- or aza-pyrimidines, pyrimidines having a substituent at the 5 or 6 positions, purine bases having a substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines; PCT No. WO 93/13121 by Cook) and "abasic" residues (i.e., no nitrogenous base for one or more backbone positions) (U.S. Pat. No. 5,585,481 to Arnold et al.) are included in the term nucleic acid. That is, a nucleic acid may comprise only conventional sugars, bases and linkages found in RNA and DNA, or may include both conventional components and substitutions (e.g., conventional bases and analogs linked via a methoxy backbone, or conventional bases and one or more base analogs linked via an RNA or DNA backbone). Another non-limiting example of a nucleic acid analog contemplated by the present invention includes bicyclic and tricyclic nucleoside and nucleotide configurations (Locked Nucleic Acids," "Locked Nucleoside Analogues" or "LNA". See Imanishi et al., U.S. Pat. No. 6,268,490; and Wengel et al., U.S. Pat. No. 6,670,461.)

The backbone of an oligomer may affect stability of a hybridization complex (e.g., formed between of a capture oligomer to its target nucleic acid). Such embodiments include peptide linkages, 2'-O-methoxy linkages and sugar-phosphodiester type linkages. Peptide nucleic acids are advantageous for forming a hybridization complex with RNA. An oligomer having 2'-methoxy substituted RNA groups or a 2'-fluoro substituted RNA may have enhance hybridization complex stability relative to standard DNA or RNA and is preferred for forming a hybridization complex with a complementary 2'-OH RNA. A linkage joining two sugar groups may affect hybridization complex stability by affecting the overall charge or the charge density, or by affecting steric interactions (e.g., bulky linkages may reduce hybridization complex stability). Preferred linkages include those with neutral groups (e.g., methylphosphonates) or charged groups (e.g., phosphorothioates) to affect complex stability.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

By "oligonucleotide" or "oligomer" is meant a nucleic acid having generally less than 1,000 residues, including polymers in a size range having a lower limit of about 5 nucleotide residues and an upper limit of about 500 nucleotide residues. Oligomers of some embodiments of the invention are in a size range having a lower limit of about 5 to about 15 residues and an upper limit of about 50 to 100 residues. Embodiments of oligomers are in a size range having a lower limit of about 10 to about 25 residues and an upper limit of about 25 to about 60 residues. These ranges are inclusive, such that all whole numbers in between are also disclosed. Oligomers may be purified from naturally occurring sources, but generally are synthesized in vitro by using any well-known enzymatic or chemical method. Generally, when an oligomer of the present invention is synthesized in vitro with a 2'-O-methoxy backbone, a uracil (U) base is used in those positions that are occupied by a thymine (T) base in the same sequence in an oligomer synthesized with sugar-phosphodiester linkages, except for a 3' T, which is a standard deoxynucleotide. That is, methoxy oligonucleotides have a methoxy group at the 2' position of the ribose moiety, and a U at the base position of a T residue in a standard DNA oligonucleotide, except when a T is present at the 3' end of the oligomer. When an oligomer is specified as containing an "OMeT" residue, a T residue occupies the base position and the backbone comprises 2'-O-methoxy linkages. Although an oligomer base sequence frequently is referred to as a DNA sequence (i.e., contains T residues), one skilled in the art will appreciate that the corresponding RNA sequence (i.e., the same base sequence but containing U in place of T), or the complementary DNA or RNA sequences are substantially equivalent embodiments of the specified DNA sequence. Indeed, as described above, an oligomer with a 2'-O-methoxy backbone may contain a mixture of U and T bases in the same oligomer.

By "amplification oligonucleotide" or "amplification oligomer" is meant an oligonucleotide, at least the 3'-end of which is complementary to a target nucleic acid, and which hybridizes to a target nucleic acid, or its complement, and participates in nucleic acid amplification. For simplicity, amplification oligomers discussed herein will refer to hybridizing to a target nucleic acid sequence. However, as is understood by those ordinarily skilled in the art, such amplification oligomers can be configured to hybridize the referenced nucleic acid sequence or the complement thereof. Examples or amplification oligomers include primers and promoter-primers. Preferably, an amplification oligonucleotide contains at least 10 contiguous bases, and more preferably at least about 12 contiguous bases but less than about 70 bases, that hybridize specifically with a region of the target nucleic acid sequence under standard hybridization conditions. The contiguous bases that hybridize to the target sequence are at least about 80%, preferably at least about 90%, and more preferably about 100% complementary to the sequence to which the amplification oligonucleotide hybridizes. An amplification oligonucleotide optionally may include modified nucleotides.

Amplification oligomers may be referred to as "primers" or "promoter-primers." A "primer" refers to an oligonucleotide that hybridizes to a template nucleic acid and has a 3' end that can be extended in a known polymerization reaction. The 5' region of the primer may be non-complementary to the target nucleic acid, e.g., the 5' non-complementary region may include a promoter sequence and the oligomer is referred to as a "promoter-primer." As used herein, a "promoter" is a specific nucleic acid sequence that is recognized by a DNA-dependent RNA polymerase ("transcriptase") as a signal to bind to the nucleic acid and begin the transcription of RNA at a specific site. Further, promoter primers may comprise blocked 3' ends to prevent their use as a primer, and in these instances, the amplification oligomer is referred to as a promoter provider. In some embodiments, blocking moieties replace an oligomer's 3' OH to prevent enzyme-mediated extension of the oligomer in an amplification reaction. In alternative embodiments a blocking moiety may be within five residues of the 3' end and is sufficiently large to limit binding of a polymerase to the oligomer. In other embodiments a blocking moiety is covalently attached to the 3' terminus of an oligomer. Many different chemical groups may be used to block the 3' end of an oligomer, including, but not limited to, alkyl groups, non-nucleotide linkers, alkane-diol dideoxynucleotide residues, and cordycepin. Those skilled in the art will further appreciate that any oligomer that can function as a primer (i.e., an amplification oligonucleotide that hybridizes specifically to a target sequence and has a 3' end that can be extended by a polymerase) can be modified to include a 5' promoter sequence, and thus function as a promoter-primer. Similarly, any promoter-primer can be modified by removal of, or synthesis without, a promoter sequence and function as a primer.

A "target nucleic acid" as used herein is a nucleic acid comprising a "target sequence" to be amplified. Target nucleic acids may be DNA or RNA as described herein, and may be either single-stranded or double-stranded. The target nucleic acid may include other sequences besides the target sequence, which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

By "isolated" it is meant that a sample containing a target nucleic acid is taken from its natural milieu, but the term does not connote any degree of purification.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during the processes of TMA. Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target binding sequence" is used herein to refer to the portion of an oligomer that is configured to hybridize with a target nucleic acid sequence. Preferably, the target binding sequences are configured to specifically hybridize with a target nucleic acid sequence. Target binding sequences may be 100% complementary to the portion of the target sequence to which they are configured to hybridize; but not necessarily. Target-binding sequences may also include inserted, deleted and/or substituted nucleotide residues relative to a target sequence. Less than 100% complementarity of a target binding sequence to a target sequence may arise, for example, when the target nucleic acid is a plurality strains within a species, such as would be the case for an oligomer configured to hybridize to the various strains and genotypes of human parvovirus. It is understood that other reasons exist for configuring a target binding sequence to have less than 100% complementarity to a target nucleic acid.

The term "targets a sequence" as used herein in reference to a region of human parvovirus nucleic acid refers to a process whereby an oligonucleotide hybridizes to the target sequence in a manner that allows for amplification and detection as described herein. In one embodiment, the oligonucleotide is complementary with the targeted human parvovirus nucleic acid sequence and contains no mismatches. In another embodiment, the oligonucleotide is complementary but contains 1; or 2; or 3; or 4; or 5 mismatches with the targeted human parvovirus nucleic acid sequence. Preferably, the oligonucleotide that hybridizes to the human parvovirus nucleic acid sequence includes at least 10 to as many as 50 nucleotides complementary to the target sequence. It is understood that at least 10 and as many as 50 is an inclusive range such that 10, 50 and each whole number there between are disclosed. Preferably, the oligomer specifically hybridizes to the target sequence. The term "configured to target a sequence" as used herein means that the target hybridizing region of an amplification oligonucleotide is designed to have a polynucleotide sequence that could specifically hybridize to the referenced human parvovirus region. Such an amplification oligonucleotide is not limited to targeting that sequence only, but is rather useful as a composition, in a kit or in a method for targeting a human parvovirus target nucleic acid including genotypes 1, 2 and/or 3, as is described herein. The term "configured to" denotes an actual arrangement of the polynucleotide sequence configuration of the amplification oligonucleotide target hybridizing sequence.

The term "region" as used herein refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a human parvovirus genome, the term "region" may be used to refer to a smaller area of the nucleic acid, wherein the smaller area is targeted by one or more oligonucleotides of the invention. The target binding sequence of an oligonucleotide may hybridize all or a portion of a region. A target binding sequence that hybridizes to a portion of a region is one that hybridizes within the referenced region. As another non-limiting example of the use of the term region, when the nucleic acid in reference is an amplicon, the term region may be used to refer to the smaller nucleotide sequence identified for hybridization by the target binding sequence of a probe.

"Amplification" refers to any known procedure for obtaining multiple copies of a target nucleic acid sequence or its complement or fragments thereof, and preferred embodiments amplify the target specifically by using sequence-specific methods. Known amplification methods include, for example, transcription-mediated amplification, replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as QB-replicase (e.g., see U.S. Pat. No. 4,786,600 to Kramer et al. and PCT No. WO 90/14439). PCR amplification is well known and uses DNA polymerase, sequence-specific primers and thermal cycling to synthesize multiple copies of the two complementary strands of DNA or cDNA (e.g., U.S. Pat. Nos. 4,683,195, 4,683,202, and 4,800,159 to Mullis et al., and *Methods in Enzymology*, 1987, Vol. 155: 335-350). LCR amplification uses at least four separate oligonucleotides to amplify a target and its complementary strand by using multiple cycles of hybridization, ligation, and denaturation (EP Patent No. 0 320 308). SDA amplifies by using a primer that contains a recognition site for a restriction endonuclease which nicks one strand of a hemimodified DNA duplex that includes the target sequence, followed by amplification in a series of primer extension and strand displacement steps (U.S. Pat. No. 5,422,252 to Walker et al.) As illustrated below, preferred embodiments use transcription-associated amplification. It will be apparent to one skilled in the art that method steps and amplification oligonucleotides of the present invention may be readily adapted to a variety of nucleic acid amplification procedures based on primer extension by a polymerase activity.

Amplification of a "fragment" or "portion" of the target sequence refers to production of an amplified nucleic acid containing less than the entire target region nucleic acid sequence. Such fragments may be produced by amplifying a portion of the target sequence, e.g., by using an amplification oligonucleotide that hybridizes to and initiates polymerization from an internal position in the target sequence.

By "transcription-mediated amplification" (TMA) or "transcription-associated amplification" is meant a nucleic acid amplification that uses an RNA polymerase to produce multiple RNA transcripts from a nucleic acid template. Transcription-associated amplification generally employs RNA polymerase and DNA polymerase activities, deoxyribonucleoside triphosphates, ribonucleoside triphosphates, and a promoter-primer, and optionally may include one or more other amplification oligonucleotides, including "helper" oligomers. Variations of transcription-associated amplification are well known in the art and described in detail elsewhere (see U.S. Pat. Nos. 5,399,491 and 5,554,516 to Kacian et al., U.S. Pat. No. 5,437,990 to Burg et al., U.S. Pat. No. 5,130,238 to Malek et al., U.S. Pat. Nos. 4,868,105 and 5,124,246 to Urdea et al., PCT No. WO 93/22461 by Kacian et al., PCT Nos. WO 88/01302 and WO 88/10315 by Gingeras et al., PCT No. WO 94/03472 by McDonough et al., and PCT No. WO 95/03430 by Ryder et al.). The procedures of U.S. Pat. Nos. 5,399,491 and 5,554,516 are preferred amplification embodiments. As used herein, the term "real-time TMA" refers to single-primer transcription-mediated amplification ("TMA") of target nucleic acid that is monitored by real-time detection means.

By "probe," "detection probe" or "detection probe oligomer" it is meant a nucleic acid oligomer that hybridizes specifically to a target sequence in a nucleic acid, preferably in an amplified nucleic acid, under conditions that allow hybridization, thereby allowing detection of the target or amplified nucleic acid. Detection may either be direct (i.e., resulting from a probe hybridizing directly to the sequence) or indirect (i.e., resulting from a probe hybridizing to an intermediate molecular structure that links the probe to the target). The probe's "target" generally refers to a sequence within or a subset of an amplified nucleic acid sequence which hybridizes specifically to at least a portion of a probe oligomer by standard hydrogen bonding (i.e., base pairing). A probe may comprise target-specific sequences and other sequences that contribute to three-dimensional conformation of the probe (e.g., U.S. Pat. Nos. 5,118,801 and 5,312,728 to Lizardi et al., and 6,361,945 B1 to Becker et al.). Probes may be DNA, RNA, analogs thereof or combinations thereof and they may be labeled or unlabeled. Probe sequences are sufficiently complementary to their target sequences if they are configured to allow stable hybridization in appropriate hybridization conditions between the probe oligomer and a target sequence that is not completely complementary to the probe's target-specific sequence.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more non-complementary residues, including abasic residues. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary, (e.g., Sambrook et al., Molecular Cloning, A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

By "preferentially hybridize" or "specifically hybridize" is meant that under stringent hybridization assay conditions, probes hybridize to their target sequences, or replicates thereof, to form stable probe: target hybrids, while at the same time formation of stable probe: non-target hybrids is minimized Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification. Appropriate hybridization conditions are well known in the art, may be predicted based on sequence composition, or can be determined by using routine testing methods (e.g., Sambrook et al., Molecular Cloning, A Laboratory Manual, 2nd ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

By "capture oligonucleotide" or "capture oligomer" or "capture probe" is meant a nucleic acid oligomer that hybridizes specifically to a target nucleic acid to be captured and provides a means for isolating and/or concentrating the target from other sample components. Embodiments of capture oligomers include two binding regions: a target-binding region and an immobilized probe-binding region, whereby the capture oligomer forms a hybridization complex in which the target-binding region of the capture oligomer binds to the target sequence and the immobilized probe-binding region binds to an oligomer immobilized on a solid support (see U.S. Pat. Nos. 6,110,678 and 6,280,952 to Weisburg et al.). Although the target-binding region and immobilized probe-binding region are usually on the same capture oligomer, the two functional regions may be present on two different oligomers joined together by one or more linkers. For example, an immobilized probe-binding region may be present on a first oligomer, a target-binding region may be present on a second oligomer, and the two oligomers are joined by hydrogen bonding with a third oligomer that is a linker that hybridizes specifically to sequences of the first and second oligomers. The target-binding region of a capture probe may also be referred to as a target-specific portion of the capture probe and the immobilized probe-binding region may be referred to as a tail portion. Embodiments of tail portions include homopolymers (e.g., poly-dT or poly-dA) or non-homopolymers (e.g., $T_{1-3}A_{30}$), preferably attached to the 3' end of the target-specific portion of the oligomer.

By "immobilized probe" or "immobilized oligomer" is meant a nucleic acid oligomer that joins, directly or indirectly, a capture oligomer to an immobilized support. An immobilized probe joined to a solid support facilitates separation of bound target sequence from unbound material in a sample. Any known solid support may be used, such as matrices and particles in solution, e.g., nitrocellulose, nylon, glass, polyacrylate, mixed polymers, polystyrene, silane polypropylene and metal particles, preferably, magnetically attractable particles. Preferred supports are monodisperse paramagnetic spheres (e.g., uniform size±5%), to provide consistent results, to which an immobilized probe is joined directly (e.g., via a direct covalent linkage, chelation, or ionic interaction), or indirectly (e.g., via one or more linkers), where the linkage or interaction is stable during nucleic acid hybridization conditions.

"Sample preparation" refers to any steps or method that treats a sample for subsequent amplification and/or detection of human parvovirus nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and PCT Pub. No. WO 2008/016988).

By "separating" or "purifying" is meant that one or more components of the biological sample are removed from at least one other component of the sample. Sample components generally include an aqueous solution of nucleic acids, salts, proteins, carbohydrates, and lipids. A step of separating or purifying a nucleic acid removes at least about 70%, preferably at least about 90% and, more preferably, at least about 95% of the other components in the sample.

By "label" is meant a molecular moiety or compound that can be detected or can lead to a detectable signal. A label is joined, directly or indirectly, to a nucleic acid probe. Direct labeling uses bonds or interactions that link the label to the probe, including covalent bonds or non-covalent interactions, such as hydrogen bonds, hydrophobic and ionic interactions, or through formation of chelates or coordination complexes. Indirect labeling uses a bridging moiety or "linker" (e.g., oligonucleotide or antibody), to link the label and probe. Linkers can be used to amplify a detectable signal. Labels are any known detectable moiety, e.g., radionuclide, ligand (e.g., biotin, avidin), enzyme or enzyme substrate, reactive group, or chromophore, such as a dye or detectable particle (e.g., latex beads or metal particles), luminescent compounds (e.g., bioluminescent, phosphorescent or chemiluminescent labels) and fluorescent compounds. Preferably, the label on a labeled probe is detectable in a homogeneous reaction (i.e., in a mixture, bound labeled probe exhibits a detectable change, such as stability or differential degradation, compared to unbound labeled probe). One embodiment of a label for use in a homogenous assay is a chemiluminescent compound (e.g., described in detail in U.S. Pat. No. 5,656,207 to Woodhead et al., U.S. Pat. No. 5,658,737 to Nelson et al., and 5,639,604 to Arnold, Jr., et al.). Preferred chemiluminescent labels are acridinium ester (AE) compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE). Synthesis and methods of attaching labels to nucleic acids and detecting labels are well known in the art (e.g., Sambrook et al., *Molecular Cloning, A Laboratory Manual*, 2nd ed. (Cold Spring Harbor Laboratory Press, Cold Spring Habor, N Y, 1989), Chapter 10; U.S. Pat. No. 4,581,333 to Kourilsky et al., U.S. Pat. No. 5,658,737 to Nelson et al., U.S. Pat. No. 5,656,207 to Woodhead et al., U.S. Pat. No. 5,547,842 to Hogan et al., U.S. Pat. No. 5,283,174 to Arnold, Jr. et al., and EP Patent Pub. No. 0747706 by Becker et al.). Another embodiment of a label for use in a homogenous assay is a fluorescent compound attached to a probe with a quencher compound in functional proximity to the fluorescent label when the probe is not hybridized to its target (e.g., U.S. Pat. Nos. 5,118,801 and 5,312,728 to Lizardi et al., and 6,361,945 B1 to Becker et al.).

A "homogeneous detectable label" refers to a label whose presence can be detected in a homogeneous fashion based upon whether the labeled probe is hybridized to a target sequence (i.e., can be detected without physically removing unhybridized label or labeled probe). Embodiments of homogeneous detectable labels and methods of detecting them have been described (U.S. Pat. No. 5,283,174 to Arnold et al., U.S. Pat. No. 5,656,207 to Woodhead et al., U.S. Pat. No. 5,658,737 to Nelson et al., U.S. Pat. Nos. 5,118,801 and 5,312,728 to Lizardi et al., and 6,361,945B1 to Becker et al.).

By "consisting essentially of" is meant that additional component(s) and method step(s)] that do not materially change the basic and novel characteristics of the present invention may be included. Such characteristics include salts, buffering agents, nucleic acid oligomers and similar biochemical reagents that do not have a material effect on the characteristics of the claimed components or method steps described herein that detect parvovirus types 1, 2 and 3 nucleic acid sequences, including nucleic amplification products derived from parvovirus types 1, 2 and 3 DNA, with a sensitivity of about 100 to 500 copies of these parvovirus DNA in the starting material. Similarly, additional method steps that do not have a material effect on the basic nature of the assay may be included.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

As used herein, an oligonucleotide that "corresponds to" or is "corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "corresponding oligonucleotides" can vary from the referred to sequence and still hybridize to the same target nucleic acid sequence. It is also understood that a first nucleic acid corresponding to a second nucleic acid includes the complements thereof and includes the RNA and DNA thereof. This variation from the nucleic acid may be stated in terms of a percentage of identical bases within the sequence or the percentage of perfectly complementary bases between the probe or primer and its target sequence. Thus, an oligonucleotide "corresponds to" a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

The term "amplicon" or the term "amplification product" as used herein refers to the nucleic acid molecule generated during an amplification procedure that is complementary or homologous to a sequence contained within the target sequence. This complementary or homologous sequence of an amplicon is sometimes referred to herein as a "target-specific sequence." Amplicons can be double stranded or single stranded and can include DNA, RNA or both. For example, DNA-dependent RNA polymerase transcribes single stranded amplicons from double stranded DNA during transcription-mediated amplification procedures. These single stranded amplicons are RNA amplicons and can be either strand of a double stranded complex; depending on how the amplification oligomers are designed. Thus, amplicons can be single stranded RNA. RNA-dependent DNA polymerases synthesize a DNA strand that is complementary to an RNA template. Thus, amplicons can be double stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double stranded DNA. RNA-dependent RNA polymerases synthesize RNA from an RNA template. Thus, amplicons can be double stranded RNA. DNA Dependent RNA polymerases synthesize RNA from double stranded DNA templates, also referred to as transcription. Thus, amplicons can be single stranded RNA Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons; all within the spirit of the current invention.

A "non-target-specific sequence," as is used herein refers to a region of an oligomer sequence, wherein said region does not stably hybridize with a target sequence under standard hybridization conditions. Oligomers with non-target-specific sequences include, but are not limited to, promoter primers, and molecular beacons. An amplification oligomer may contain a sequence that is not complementary to the target or template sequence; for example, the 5' region of a primer may include a promoter sequence that is non-complementary to the target nucleic acid (referred to as a "promoter-primer"). Those skilled in the art will understand that an amplification oligomer that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

As used herein, the term "relative light unit" ("RLU") is an arbitrary unit of measurement indicating the relative number of photons emitted by the sample at a given wavelength or band of wavelengths. RLU varies with the characteristics of the detection means used for the measurement.

The term "specificity," in the context of an amplification and/or detection system, is used herein to refer to the characteristic of the system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio). In terms of detection, specificity generally refers to the ratio of signal produced from target nucleic acids to signal produced from non-target nucleic acids.

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

Assays of the present invention detect human parvovirus present in a biological sample (e.g., blood, serum, plasma, sputum, bronchial lavage). In one embodiment, the assay detected parvovirus DNA in plasma samples that are from individual donors, or from a pooled collection of donor samples. To prepare plasma specimens, whole blood samples were centrifuged using standard methods, and the plasma was stored at 4.deg. C. or –20.deg. C. before testing. To lyse viral particles in the specimen, a lysing reagent containing a detergent was mixed with the specimen to release the parvovirus DNA from viral particles. Specimen processing may combine viral lysis with purification of the viral target DNA by including a capture oligomer and immobilized oligomer in the lysing reagent. Then the method includes a target capture step in which the parvovirus DNA is hybridized specifically to the capture oligomer, which is then hybridized to the immobilized oligomer, and the bound complex (i.e., immobilized oligomer, capture oligomer, and viral target DNA) is substantially separated from other sample components. Washing the solid support with the bound parvovirus-containing complex washes residual sample components away. Thus, the viral target DNA is separated from other sample components and concentrated in the bound complexes, without releasing the bound parvovirus nucleic acid from the solid support.

Typical sample processing involved the following steps (described in detail in U.S. Pat. No. 6,110,678). Viral particles in body fluid (e.g., 0.5 ml of plasma) were lysed upon contact at 60.deg. C. with target capture reagent (790 mM HEPES, 680 mM LiOH, 10% lithium lauryl sulfate (LLS), 230 mM succinate, at least one capture probe at 7 pm/ml, and 100 µg/ml of poly-dT$_{14}$ bound to magnetic particles (SERADYN™, Indianapolis, Ind.)). Capture oligomers comprised a 5' target-binding region sequence (e.g., SEQ ID NOs. 1, 2, 20, 21 and 53). Capture oligomers further comprised homopolymer or non-homopolymer 3' tail sequence that hybridizes to the complementary oligomer attached to the solid support (e.g., an oligo-dT attached to a solid support and an oligo-dA tail portion of a capture oligomer). Other preferred embodiments of capture probes are oligomers comprising a 5' target-binding sequence of 27 to 33 nucleotides in length that contains SEQ ID NO:41 and that further comprise an immobilized probe-binding region sequence at its 3' end. Still other preferred embodiments of capture probes comprise a 5' target-binding sequence that is configured to bind specifically to a region of a human parvovirus nucleic acid, said region corresponding to residues 2505 to 2532 of SEQ ID NO:90 (SEQ ID NO:22) and that further comprise an immobilized-probe binding region sequence at its 3' end. Another preferred embodiment comprises a 5' target-binding sequence that is configured to bind specifically to a region within a target sequence of a human parvovirus nucleic acid, said region corresponding to residues 2065 to 2101 of GenBank Accession No. DQ225149.1 gi:77994407 (SEQ ID NO:29) and further comprises a 3' immobilized-probe binding region. Target capture hybridization occurs in this reaction mixture by incubating the mixture at a first temperature (60.deg. C.), allowing the capture oligomer to bind specifically to its complementary target sequence in a parvovirus DNA. Then, the mixture was cooled to 40.deg. C. or lower (e.g., room temperature) to allow the 3' tail of the capture oligomer to hybridize to its complementary oligomer on the particle. Following the second hybridization, the mixture is treated to separate the solid support with its bound complex of nucleic acids from the other sample components, e.g., by using gravitational, centrifugal, or magnetic separation. Generally, separation employed a rack containing a magnet to pull the magnetic particles with bound nucleic acid complexes to the side of the tube. Then the supernatant was removed and the bound complexes on the particles were washed with 1 ml of a washing buffer (10 mM HEPES, 6.5 mM NaOH, 1 mM EDTA, 0.3% (v/v) absolute ethanol, 0.02% (w/v) methyl paraben, 0.01% (w/v) propyl paraben, 150 mM NaCl, 0.1% sodium dodecyl sulfate (SDS), pH 7.5) by suspending the magnetic particles in washing buffer, separating particles to the tube side, and removing the supernatant.

Following sample preparation, amplification of the parvovirus DNA target was achieved by using amplification oligomers that define the 5' and 3' ends of the region amplified by in vitro enzyme-mediated nucleic acid synthesis to generate an amplicon. One embodiment uses a transcription-mediated amplification (TMA) method, substantially as described in U.S. Pat. Nos. 5,399,491 and 5,554,516, which is a substantially isothermal system that produces a large number of amplification products (RNA transcripts) that can be detected. Preferred embodiments of the method used mixtures of amplification oligomers in which at least one promoter primer is combined with at least one primer.

A preferred embodiment of amplification oligomer combinations comprises a primer oligomer member and a promoter-based oligomer member. Preferably, a promoter-based amplification oligomer is a promoter primer comprising a 5' RNA polymerase promoter sequence and a 3' target binding sequence. RNA polymerase promoter sequences are known in the art to include, but not be limited to, sp6 RNA polymerase promoter sequences, T3 RNA polymerase promoter sequences and T7 RNA polymerase promoter sequences. In the preferred embodiments, a promoter primer comprises a 5' T7 RNA polymerase promoter sequence and a 3' target binding sequence. Most preferably, the 5' T7 RNA polymerase promoter sequence is SEQ ID NO:19.

In one preferred embodiment, the 3' target binding sequence of a promoter-based amplification oligomer is from about 10 to about 40 nucleobases in length and comprises a nucleic acid sequence that is configured to specifically hybridize to a region within a target sequence of a human parvovirus nucleic acid, wherein said region is from residue 2428 to residue 2438 of GenBank Accession Number DQ225149.1, gi:77994407. GenBank Accession Number DQ225149.1, gi:77994407 is referenced herein as SEQ ID NO:90, and the region corresponding to from residue 2428 to residue 2438 thereof is referenced herein as SEQ ID NO:83. Promoter-based oligomer members of the current invention are described herein. These descriptions need not be repeated here. Some particularly preferred promoter primers are SEQ ID NOS:56, 76, 66, 23, 81, 72 and 61. Other preferred promoter primers comprise an internal tag sequence, which is flanked on its 5' end by a promoter sequence, and on its 3' end by a target binding sequence. Internal tag sequences are also referred to herein as insert sequences. An internal tag sequence is any nucleic acid sequence that preferably does not stably hybridize with the target nucleic acid or interfere with the target binding sequence hybridizing with the target nucleic acid. Moreover, an internal tag sequence is preferably of a sufficient length and composition such that once incorporated into an amplification product, a tag-specific amplification oligomer can be used to participate in subsequent rounds for generating amplification product. One preferred tag sequence is from about 10 nucleotides in length to about 50 nucleotides in length. Another preferred tag sequence is about 12 nucleotides in length. A further preferred tag sequence is about 12 nucleotides in length and comprises the nucleotide sequence 5'-CCTACGATGCAT-3' (SEQ ID NO:94). A preferred tag sequence is SEQ ID NO:94. Another preferred tag sequence is about 20 nucleotides in length. A further preferred tag sequence is about 20 nucleotides in length and comprises the nucleotide sequence 5'-GTCATATGCGACGATCTCAG-3' (SEQ ID NO:95). A preferred tag sequence is SEQ ID NO:95. Particularly preferred promoter primers comprising a 3' target binding sequence, and internal tag sequence and a 5' promoter sequence are SEQ ID NOS:63, 73, 67, 68, 78, 82 and 58. Ordinarily skilled artisans will recognize that the design of a tag sequence and its incorporation into an amplification oligomer of the current invention can follow any of a number of design strategies, while still falling within the objectives and advantages described herein. Moreover, it is recognized that insert sequences can be included with any of the promoter-based oligomer members of the current invention.

In a preferred embodiment, the amplification oligomer combination comprises at least one primer amplification oligomer member. Preferred primer amplification oligomers have a length that is from about 10 nucleobases to about 50 nucleobases, and have a nucleotide composition configured to specifically hybridize with human parvovirus types 1, 2 and 3 to generate a detectable amplification product when used in an amplification reaction of the current invention. One preferred primer oligomer is from about 10 to about 50 nucleobases in length and has a target binding sequence that is configured to specifically hybridize all or a portion of a region of a target sequence of a human parvovirus nucleic acid, wherein said region corresponds to from residue 2304 to residue 2332 of GenBank Accession Number DQ225149.1, gi:77994407 (SEQ ID NO:96). Primer oligomer members of the current invention are described herein. These descriptions need not be repeated here. Particularly preferred primer oligomer members are selected from the group consisting of SEQ ID NOS:18, SEQ ID NO:48; SEQ ID NO:50 and SEQ ID NO:96. One particularly preferred primer oligomer member comprises a target-binding sequence that is SEQ ID NO:50. Another particularly preferred primer oligomer member comprises a target binding sequence that is SEQ ID NO:48. Other preferred primer oligomer members comprise a 5' tag sequence. An 5' tag sequence is any nucleic acid sequence that preferably does not stably hybridize with the target nucleic acid or interfere with the target binding sequence hybridizing with the target nucleic acid. Moreover, a 5' tag sequence is preferably of a sufficient length and composition such that once incorporated into an amplification product, a tag-specific amplification oligomer can be used to participate in subsequent rounds for generating amplification product. One preferred 5' tag sequence is from about 10 nucleotides in length to about 50 nucleotides in length. Another preferred tag sequence is about 12 nucleotides in length. A further preferred tag sequence is about 12 nucleotides in length and comprises the nucleotide sequence 5'-CCTACGATGCAT-3' (SEQ ID NO:94). A preferred tag sequence is SEQ ID NO:94. Another preferred tag sequence is about 20 nucleotides in length. A further preferred tag sequence is about 20 nucleotides in length and comprises the nucleotide sequence 5'-GTCATATGCGACGATCTCAG-3' (SEQ ID NO:95). A preferred tag sequence is SEQ ID NO:95. Particularly preferred primer oligomer members with a 5' tag sequence are SEQ ID NOS:47 & 49. Ordinarily skilled artisans will recognize that the design of a tag sequence and its incorporation into an amplification oligomer of the current invention can follow any of a number of design strategies, while still falling within the objectives and advantages described herein. Moreover, it is recognized that 5' tag sequences can be included with any of the primer oligomer members of the current invention.

Amplifying the target nucleic acid by transcription-mediated amplification produces many strands of nucleic acid from a single copy of target nucleic acid, thus permitting detection of the target by detecting probes that hybridize to the sequences of the amplification product. Generally, the reaction mixture includes the target nucleic acid and at least two amplification oligomers comprising at least one primers, at least one promoter primer, reverse transcriptase and RNA polymerase activities, nucleic acid synthesis substrates (deoxyribonucleoside triphosphates and ribonucleoside triphosphates) and appropriate salts and buffers in solution to produce multiple RNA transcripts from a nucleic acid template. Briefly, a promoter-primer hybridizes specifically to a portion of the target sequence. Reverse transcriptase that includes RNase H activity creates a first strand cDNA by 3' extension of the promoter-primer. The cDNA is hybridized with a primer downstream from the promoter primer and a new DNA strand is synthesized from the 3' end of the primer using the reverse transcriptase to create a dsDNA having a functional promoter sequence at one end. RNA polymerase binds to dsDNA at the promoter sequence and transcribes multiple transcripts or amplicons. These amplicons are further used in the amplification process, serving as a template for a new round of replication, to ultimately generate large amounts of single-stranded amplified nucleic acid from the initial target sequence (e.g., 100 to 3,000 copies of RNA synthesized from a single template). The process uses substantially constant reaction conditions (i.e., substantially isothermal). A typical 100 µl amplification reaction uses 75 µl of an amplification reagent mixture (11.6 mM Tris Base, 15.0 mM Tris-HCl, 22.7 mM $MgCl_2$, 23.3 mM KCl, 3.33% glycerol, 0.05 mM Zn-acetate (dihydrate), 0.665 mM each of dATP, dCTP, dGTP, and dTTP, 5.32 mM each of ATP, CTP, GTP, and UTP, pH 7) and 25 µl of an enzyme reagent mixture (700 U of T7 RNA polymerase, 1400 U of reverse transcriptase from Moloney Murine Leukemia Virus (MMLV-RT), 16 mM HEPES (free acid, dihydrate), 70 mM N-acety-L-cysteine, 3 mM EDTA, 0.05% (w/v) Na-azide, 20 mM Tris base, 50 mM KCl, 20% (v/v) anhydrous glycerol, 10% (v/v) TRITON® X-102, and 150 mM trehalose (dihydrate), pH 7), preferably mixed with the captured target nucleic acid retained on the solid particles. For the enzymatic activities, 1 U of T7 RNA polymerase incorporates 1 nmol of ATP into RNA in 1 hr at 37.deg. C. using a DNA template containing a T7 promoter, and 1 U of MMLV-RT incorporates 1 nmol of dTTP into DNA in 10 min at 37.deg. C. using 200-400 µmol oligo dT-primed poly(A) as a template.

In one preferred embodiment, a TMA reaction is performed using a combination of amplification oligomers, wherein said combination comprises at least one promoter primer oligomer member and at least one primer oligomer member, and wherein said combination is configured to generate amplification products for the detection of human parvovirus types 1, 2 and 3. In an aspect of this embodiment, the amplification oligomer combination comprises at least one promoter primer oligomer member comprising a 5' promoter sequence, an internal tag sequence and a 3' target binding sequence. In an aspect of this embodiment, the amplification oligomer combination comprises at least one promoter primer oligomer member comprising a 5' promoter sequence, an internal tag sequence and a 3' target binding sequence, and also comprises at least one promoter primer oligomer member comprising a 5' promoter sequence and a 3' target binding sequence. In an aspect of this embodiment, the amplification oligomer combination comprises at least one primer oligomer member comprising a 5' tag sequence and a 3' target binding sequence. In an aspect of this embodiment, the amplification oligomer combination comprises at least one primer oligomer member comprising a 5' tag sequence and a 3' target binding sequence, and also comprises at least one primer oligomer member comprising a 3' target binding sequence.

In another preferred embodiment, the TMA reaction is performed with an amplification oligomer combination comprising at least one promoter primer oligomer member and at least one primer oligomer member, wherein configured to generate amplification products for the detection of human parvovirus types 1, 2 and 3, and wherein said amplification oligomer combination is configured to generate from GenBank Accession No DQ225149.1 gi:77994407 an amplicon that is about 100 nucleobases in length to about 225 nucleobases in length and comprises a target specific sequence that contains SEQ ID NO:39. As is discussed herein, and thus will not be repeated in detail here, amplicons generated using the amplification oligomer combinations of the current invention amplicons comprise, for example, target sequences containing SEQ ID NOS:25, 26, 39, 86, 97, 88, 89, 98, 99, 100 and combinations thereof. Ordinarily skilled artisans will recognize that the design of an amplification reaction using an amplification oligomer combination can include primer pairs, promoter-based amplification oligomer pairs or one or more primer members combined with one or more promoter-based amplification oligomer members, and can be any type of amplification reaction, while still falling within the objectives and advantages described herein. Further, ordinarily skilled artisans will recognize that an amplification oligomer combination can be configured to generate from SEQ ID NO:90, amplicons that are larger or smaller than what is illustrated here, and such amplicons will fall within the objectives and advantages described herein.

Following amplification, the amplified sequences generated from the parvovirus DNA are detected, preferably by hybridization with at least one labeled nucleic acid probe that hybridizes specifically to a portion of the amplified sequence. Probe embodiments include those having a $T_m$ in the range of about 80.deg. C. to about 85.deg. C. Some preferred probe embodiments include oligomers having a nucleotide length of from about 15 to about 40 nucleotides and a nucleic acid sequence that is DNA, RNA or a combination there of and is configured to specifically hybridize with all or a portion of a region of a target sequence of a human parvovirus nucleic acid or amplified nucleic acid, said region being from residue 2376 to residue 2409 of GenBank Accession Number DQ225149.1, gi:77994407 (SEQ ID NO:33). Detection probe oligomers of the current invention are described herein. These descriptions need not be repeated here. Particularly preferred probe embodiments include oligomers selected from the group consisting of SEQ ID NO:28, SEQ ID NO:30, SEQ ID NO:31, SEQ ID NO:32, SEQ ID NO:42, SEQ ID NO:43, SEQ ID NO:44 and SEQ ID NO46. Preferably, detection oligomers of the current invention further comprise one or more LNA residues. Detection of the probe is preferably accomplished by detecting a label that can be detected in a homogeneous reaction. Therefore, some preferred embodiments further comprise probes labeled with an acridinium ester (AE) compound using well-known methods that allow homogeneous detection (e.g., labels and detection methods are described in detail in U.S. Pat. No. 5,283,174 to Arnold, Jr., et al., U.S. Pat. No. 5,656,207 to Woodhead et al., and 5,658,737 to Nelson et al.). A chemiluminescent AE compound is attached to the probe sequence via a linker compound (substantially as described in U.S. Pat. Nos. 5,585,481 and 5,639,604 to Arnold, Jr., et al., e.g., see column 10, line 6 to column 11, line 3, and Example 8). In one embodiment, the labeled probe oligomer has at least one 2'-O-methoxy linkage in the nucleic acid backbone. In a typical detection step, the probe reagent included 100 mM succinate, 2% (w/v) LLS, 230 mM LiOH (monohydrate), 15 mM 2,2'-dithiodipyridine (ALDRITHIOL-2), 1.2 M LiCl, 20 mM EDTA, 20 mM EGTA, 3% (v/v) absolute ethanol, brought to about pH 4.7 with LiOH, and the selection reagent used for hydrolyzing the label on unbound probe included 600 mM boric acid, 182 mM NaOH, 1% (v/v) TRITON® X-100. The signal was detected as relative light units (RLU) using a luminometer (e.g., LEADER™ 450HC+, Gen-Probe Incorporated, San Diego, Calif.).

To select DNA sequences appropriate for use as capture oligomers, amplification oligomers and detection probes, known parvovirus types 1, 2 and 3 DNA sequences, including partial or complementary sequences, available from publicly accessible databases (e.g., GenBank) were aligned by matching regions of the same or similar sequences and compared using well known molecular biology techniques. Although sequence comparisons may be facilitated by use of algorithms, those skilled in the art can readily perform such comparisons manually and visually. Generally, portions of sequences that contain relatively few variants between the compared sequences were chosen as a basis for designing synthetic oligomers for use in the present invention. Other considerations in designing oligomers included the relative GC content (which affects $T_m$) and the relative absence of predicted secondary structure (which potentially form intramolecular hybrids) within a sequence, as determined by using well-known methods.

In one embodiment, the assay is carried out in a single tube using a 0.5 to 1 ml sample of body fluid (e.g., plasma) to detect target parvovirus DNA at a sensitivity of about 100 to 500 copies/ml of target DNA per reaction. In other embodiments, the assay detected higher numbers of target parvovirus DNA in the sample, which may be a pooled sample of individual samples.

Unless defined otherwise, all scientific and technical terms used herein have the same meaning as commonly understood by those skilled in the relevant art. General definitions of many of the terms used herein are provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and *Taber's Cyclopedic Medical Dictionary*, 17th ed. (F.A. Davis Co., Philadelphia, Pa., 1993). Unless mentioned otherwise, the techniques employed or contemplated herein are standard methodologies well known to one of ordinary skill in the art. The following examples illustrate some of the preferred embodiments of the invention and are provided for illustration only.

Example 1: Target Capture of Parvovirus DNA

Capture probes were synthesized by standard in vitro DNA synthesis reactions having sequences of SEQ ID NO:1, SEQ ID NO:2, SEQ ID NO:20, SEQ ID NO:21 and SEQ ID NO: 52, all having 3' $dA_{30}$ tail portions or a 3' $dT_3$, $dA_{30}$ tail portions. In a first experiment, SEQ ID NOS:1 and 2 were separately assayed for capture of a human parvovirus from plasma. Using the target capture methods described above, the capture oligomers were mixed with human plasma samples obtained from uninfected donors, each sample was spiked with a known number of copies of live parvovirus B19 (2,000, 1,000, 500 or 0 in the negative control). The virions were lysed by mixing the plasma sample (generally 0.5 ml) with an equal volume of target capture reagent containing each of the capture probes separately (3.5 pmol per reaction). Following capture by hybridization at about 60.deg. C. for about 20 min and then at 18-25.deg. C. for about 10-20 min, the magnetic particles with attached hybridization complexes were washed twice as described above. The parvovirus target sequence in the complexes retained on the particles was amplified in a TMA reaction performed substantially as described herein and in Example 2, and the amplified target sequences were detected by hybridization with an AE-labeled probe (SEQ ID NO:17). The results (RLU detected from bound detection probe) are shown in Table 1. These results (RLU of about 1.5×10.sup.6) show that both capture probes specifically bind to and effectively capture parvovirus DNA from a sample compared to the negative control (RLU about 2×10.sup.4).

TABLE 1

Detection of labeled probe (RLU) bound to parvovirus DNA following target capture.

| B19 copies per reaction | $A_{30}$ Capture Probe SEQ NO: 1 | $A_{30}$ Capture Probe SEQ NO: 2 |
|---|---|---|
| 2,000 | 1.56 × 10.sup.6 | 1.61 × 10.sup.6 |
| 1,000 | 1.42 × 10.sup.6 | 1.53 × 10.sup.6 |
| 500 | 1.58 × 10.sup.6 | 1.59 × 10.sup.6 |
| 0 | 1.98 × 10.sup.4 | 2.44 × 10.sup.4 |

In a second target assay, SEQ ID NOS:1, 20 and 21 target capture oligomers were assayed separately and in combination for capture of human parvovirus type 1 from plasma. Reactions included each of SEQ ID NOS 1, 20 and 21 individually, and in the various possible combinations (SEQ ID NOS 1 and 20, SEQ ID NOS 1 and 21, SEQ ID NOS 20 and 21, and SEQ ID NOS 1, 20 and 21). Plasma sample containing parvovirus type 1 were mixed with a lysing reagent and a capture reagent containing one or more of the capture oligomers at 3.5 pmol each per reaction and were incubated and hybridized as discussed above. Following separation and wash the attached hybridization complexes were incubated in a TMA amplification mixture containing 15 pmol per reaction of each of SEQ ID NO:23 and SEQ ID NO:13, and the appropriate salts, nucleotides and enzymes. Detection was performed using SEQ ID NO:17 labeled with 2-methyl-AE between nt 7 and nt 8 and the chemiluminescent signal was detected (RLU) as described in detail previously (U.S. Pat. Nos. 5,283,174, 5,656,207, and 5,658,737).

The tested human plasma samples contained either no parvovirus (negative samples) or 1,000 copies per reaction of parvovirus (positive samples), which were prepared by dilution from a stock sample of infected plasma (from the American Red Cross) that had been titrated by comparison with a standardized sample (IS 99/800 from National Institute for Biological Standards and Control, "NIBSC," Hertfordshire, England). Ten replicate samples were tested for each of the conditions. The detected results (RLU mean±standard deviation) are shown in Table 2.

TABLE 2

Results of Assays Performed Using Different Capture Oligomers.

| Capture Oligomers | Negative Samples | Positive Samples |
|---|---|---|
| SEQ ID NO: 1 | 2,461 ± 1,252 | 4,067,173 ± 163,492 |
| SEQ ID NO: 20 | 2,137 ± 360 | 3,893,205 ± 477,513 |
| SEQ ID NO: 21 | 4,774 ± 6,970 | 3,954,416 ± 468,324 |
| SEQ ID NOS: 1 and 20 | 5,285 ± 4,911 | 4,078,141 ± 269,686 |
| SEQ ID NO: 1 and 21 | 2,560 ± 1,002 | 4,093,581 ± 271,294 |
| SEQ ID NO: 20 and 21 | 2,164 ± 301 | 4,000,996 ± 361,454 |
| SEQ ID NO: 1, 20 and 21 | 4,291 ± 4,919 | 3,994,533 ± 116,348 |

The target capture oligomer combinations were tested again, this time the plasma samples contained no parvovirus (negative samples) or varying amounts of parvovirus (1,000, 500, 250, 100 and 50 copies per reaction), prepared by dilution from the stock sample described above. For each of the conditions, five replicate samples were tested for those containing 1,000 and 0 copies of parvovirus B19, and ten replicate samples were tested for all the others. The detected results (RLU mean±standard deviation) are shown below in Table 3. For all of the negative controls (0 copies per reaction), the detected background was in the range of 2,277±215 to 4,724±3,889 RLU.

TABLE 3

Sensitivity of Assays Performed Using Different Capture Oligomers

| SEQ ID NOS | Copies of Parvovirus Per Reaction | | | | |
|---|---|---|---|---|---|
| | 1,000 | 500 | 250 | 100 | 50 |
| 1 | 4.04 × 10.sup.6 ± 4.18 × 10.sup.5 | 3.80 × 10.sup.6 ± 5.01 × 10.sup.5 | 3.55 × 10.sup.6 ± 8.04 × 10.sup.5 | 1.89 × 10.sup.6 ± 1.55 × 10.sup.6 | 8.04 × 10.sup.5 ± 1.34 × 10.sup.6 |
| 20 | 4.00 × 10.sup.6 ± 3.60 × 10.sup.5 | 3.89 × 10.sup.6 ± 5.63 × 10.sup.5 | 2.78 × 10.sup.6 ± 1.22 × 10.sup.5 | 2.06 × 10.sup.6 ± 1.59 × 10.sup.6 | 1.85 × 10.sup.6 ± 1.73 × 10.sup.5 |
| 21 | 4.27 × 10.sup.6 ± 5.85 × 10.sup.4 | 4.00 × 10.sup.6 ± 3.22 × 10.sup.5 | 3.25 × 10.sup.6 ± 1.24 × 10.sup.6 | 1.26 × 10.sup.6 ± 1.05 × 10.sup.6 | 7.13 × 10.sup.5 ± 1.28 × 10.sup.6 |
| 1 & 20 | 4.14 × 10.sup.6 ± 1.71 × 10.sup.6 | 3.51 × 10.sup.6 ± 1.34 × 10.sup.5 | 3.57 × 10.sup.6 ± 9.30 × 10.sup.5 | 2.10 × 10.sup.6 ± 1.66 × 10.sup.6 | 1.13 × 10.sup.6 ± 1.52 × 10.sup.6 |
| 1 & 21 | 4.28 × 10.sup.6 ± 8.45 × 10.sup.4 | 3.78 × 10.sup.6 ± 1.16 × 10.sup.6 | 3.23 × 10.sup.6 ± 1.08 × 10.sup.6 | 1.60 × 10.sup.6 ± 1.33 × 10.sup.6 | 1.44 × 10.sup.6 ± 1.60 × 10.sup.6 |
| 20 & 21 | 4.15 × 10.sup.6 ± 2.10 × 10.sup.5 | 4.26 × 10.sup.6 ± 1.49 × 10.sup.5 | 2.68 × 10.sup.6 ± 1.76 × 10.sup.6 | 1.55 × 10.sup.6 ± 1.69 × 10.sup.6 | 1.06 × 10.sup.6 ± 1.28 × 10.sup.6 |

TABLE 3-continued

Sensitivity of Assays Performed Using Different Capture Oligomers

| SEQ ID NOS | Copies of Parvovirus Per Reaction | | | | |
|---|---|---|---|---|---|
| | 1,000 | 500 | 250 | 100 | 50 |
| 1, 20 & 21 | $4.24 \times 10^6 \pm 1.30 \times 10^5$ | $4.35 \times 10^6 \pm 1.09 \times 10^5$ | $2.56 \times 10^6 \pm 1.59 \times 10^6$ | $2,529,303 \pm 1,652,537$ | $9.62 \times 10^5 \pm 1.46 \times 10^6$ |

The results of these experiments show that when the assay was performed with any of these three capture oligomers, alone or in a mixture, each format detected the presence of parvovirus B19. The assays resulted in positive signals for all samples that contained 250 to 1,000 copies/ml, for 80 to 90% of samples that contained 100 copies/ml, and for 50 to 70% of samples that contained 50 copies/ml.

Example 2: Detection of Parvovirus in an Amplification Assay that Uses Target Capture In this example, the target capture assay was performed substantially as described in Example 1 using SEQ ID NO:1 or SEQ ID NO:2. Amplification and detection steps were performed substantially as follows. A known amount of parvovirus type 1 target nucleic acid (denatured ssDNA at 500, 250, 100, 50 and 0 copies per reaction tube) was amplified in a TMA reaction using reagents (75 µl per reaction) as described above containing a promoter primer of SEQ ID NO:3 with a primer of SEQ ID NO:13 or a promoter primer of SEQ ID NO:5 with a primer of SEQ ID NO:13 (7.5 pmol each amplification oligomer member per reaction). The mixture was incubated 10 min at 60.deg. C., then 10 min at 42.deg. C. Then 25 µl of enzyme reagent was added and the tubes were mixed by hand and then incubated 60 min at 42.deg. C. Following amplification the samples were incubated at 60.deg. C. and 100 µl of probe reagent containing probe of SEQ ID NO:17 was added. The mixture was incubated 20 min at 60.deg. C. and then 300 µl of selection reagent was added, mixed, and incubated 10 min at 60.deg. C. and 10 min at room temperature before detecting the signal (RLU) as described above. The results shown in Table 4 are for an average of 5 samples for each of the conditions tested. These results show that the sensitivity of the assay is about 250 copies of target parvovirus type 1 DNA in the sample or better (i.e., capable of detecting 100 copies per sample). The primer set of SEQ ID NO:3 plus SEQ ID NO:13 had sensitivity of better than 250 copies of virus in capture from plasma, as well has stable, reproducible signal with 100 copies sensitivity in an amplification and detection assay.

Example 3: Amplification of Parvovirus Sequences Using Various Amplification Oligomers This example shows that different combinations of amplification oligomers serving as primers can efficiently amplify the target sequences in parvovirus DNA. The target sequences were amplified by using a combination of primers that had the target specific sequence of SEQ ID NO:24, SEQ ID NO:4 and SEQ ID NO:13. SEQ ID NOS:24 and 4 further comprised the promoter sequence SEQ ID NO:19. Samples were prepared by mixing human plasma that does not contain parvovirus (negative control) with aliquots of parvovirus to produce samples containing 10,000, 5,000, 1,000, 500, 250, 100, 50, and 25 copies of parvovirus per ml. As a positive control, standard samples containing 1,000 copies of parvovirus per ml were also assayed. The samples were first mixed with a target capture oligomer (SEQ ID NO:1) which was allowed to hybridize to the parvovirus DNA, and then the hybridization complex containing the parvovirus DNA was separated from the sample by hybridizing it to an oligomer attached to a magnetic bead, substantially as described previously (U.S. Pat. No. 6,110,678).

The amplification assays were performed using the TMA system substantially as described above. The amplification reaction contained 15 pmol each of the promoter primer of SEQ ID NO:23 and the primer of SEQ ID NO:13, or 15 pmol each of the promoter primer of SEQ ID NO:3 and the primer of SEQ ID NO:13. Following the one-hour amplification reaction, the mixtures were hybridized with a detection probe of SEQ ID NO:17 labeled with a chemiluminescent compound between nt 7 and 8 (using $5.5 \times 10^9$ RLU per reaction), and the relative light unit (RLU) signals were detected as described above. For the positive and negative controls, 5 replicate samples were tested. For the experimental samples, 10 replicates were tested for each condition. The results of these assays (RLU mean±standard deviation) are shown in Table 5.

TABLE 4

Detected signal (RLU) for target capture plus amplification assays.

| Oligomers SEQ ID NOS: | | Copies of Parvovirus Type 1 | | | |
|---|---|---|---|---|---|
| Capture | Amp | 500 | 250 | 100 | 0 |
| 1 | 3 & 13 | $1.30 \times 10^6$ | $1.30 \times 10^6$ | $9.86 \times 10^5$ | $3.30 \times 10^4$ |
|   | 5 & 13 | $2.37 \times 10^6$ | $2.91 \times 10^5$ | $2.52 \times 10^5$ | $4.66 \times 10^4$ |
| 2 | 3 & 13 | $9.65 \times 10^5$ | $8.88 \times 10^5$ | $7.85 \times 10^5$ | $1.15 \times 10^5$ |
|   | 5 & 13 | $2.06 \times 10^5$ | $1.03 \times 10^5$ | $4.14 \times 10^4$ | $3.51 \times 10^3$ |

TABLE 5

Assay Results Obtained Using Various Amplification Oligomers

| Parvovirus B19 copies/ml | SEQ ID NO: 13 and SEQ ID NO: 23 Primers | SEQ ID NO: 13 and SEQ ID NO: 3 Primers |
|---|---|---|
| 1,000 (positive control) | $3.87 \times 10^6 \pm 1.89 \times 10^5$ | $2.53 \times 10^6 \pm 7.94 \times 10^5$ |
| 10,000 | $4.20 \times 10^6 \pm 8.27 \times 10^4$ | $4.03 \times 10^6 \pm 7.29 \times 10^5$ |
| 5,000 | $4.07 \times 10^6 \pm 2.73 \times 10^5$ | $3.97 \times 10^6 \pm 1.15 \times 10^5$ |
| 1,000 | $3.80 \times 10^6 \pm 7.38 \times 10^5$ | $2.77 \times 10^6 \pm 6.63 \times 10^5$ |
| 500 | $3.17 \times 10^6 \pm 1.09 \times 10^6$ | $1.82 \times 10^6 \pm 1.13 \times 10^6$ |
| 250 | $2.90 \times 10^6 \pm 7.57 \times 10^5$ | $1.07 \times 10^6 \pm 5.83 \times 10^5$ |
| 100 | $1.73 \times 10^6 \pm 1.54 \times 10^6$ | $3.79 \times 10^5 \pm 4.73 \times 10^5$ |
| 50 | $1.74 \times 10^6 \pm 1.74 \times 10^4$ | $2.34 \times 10^5 \pm 5.96 \times 10^5$ |
| 25 | $2.20 \times 10^5 \pm 5.66 \times 10^5$ | $2.52 \times 10^5 \pm 7.83 \times 10^5$ |
| 0 (negative control) | $2.73 \times 10^3 \pm 5.12 \times 10^2$ | $3.57 \times 10^3 \pm 2.37 \times 10^3$ |

The results show that both combinations of oligomers used as primers performed substantially equally in the assay to amplify parvovirus sequences. In both assay formats, positive signals were detected for all of the samples containing 250 or more copies of parvovirus B19, and positive signals were detected for 70 to 80% of the samples containing 100 copies.

Example 4: Parvovirus Detection Assays Performed with Various Detection Probes In this example, parvovirus was assayed by using substantially the method described in Example 2. Briefly, samples were prepared using human plasma that contains no parvovirus (negative control), by adding known amounts of parvovirus (to achieve final concentrations of 10,000, 5,000, 1,000, 500, 250, 100, 50, and 25 copies per ml). Previously tested known samples containing 1,000 copies of parvovirus per ml were included as positive controls. Samples were assayed by first capturing the parvovirus DNA from a 1 ml sample by hybridization to a complementary oligomer (SEQ ID NO:1) which was then hybridized via its 3' poly(A) tail to a complementary poly(T)-oligomer attached to magnetic beads using procedures substantially as described. Then, a target portion of the parvovirus genomic sequence was amplified in a one-hour TMA reaction using a promoter primer of SEQ ID NO:23 (comprising the target-specific sequence of SEQ ID NO:24 and a T7 RNA polymerase promoter sequence of SEQ ID NO:19) and a primer of SEQ ID NO:13. The amplification products were detected by using detection probes labeled with 2-methyl-AE in a reaction to detect relative light units (RLU) as described in detail previously (U.S. Pat. Nos. 5,585,481 and 5,639,604). The detection probes were synthesized by using standard chemical methods to produce oligomers with a 2'-O-methoxy backbone and having the nucleotide sequences of SEQ ID NO:17 (label between nt 7 and 8), SEQ ID NO:27 (label between nt 5 and 6), and SEQ ID NO:28 (label between nt 9 and 10). Two separate sets of assays were performed, one in which the detection results were obtained by using SEQ ID NOS:17 and 27, and another in which detection results were obtained by using SEQ ID NOS:17 and 28 (using $1 \times 10^6$ RLU per reaction in both sets of assays). Ten replicate samples were assayed for each of the experimental conditions, and five replicate samples were assayed for the positive (1,000 copies) and negative (0 copies) controls and the NIBSC standard (1,000 genome equivalents/ml). The results of these tests (detected RLU mean±standard deviation) are shown in Table 6.

TABLE 6

Detection of Amplified Parvovirus Target Sequences Using Various Detection Probes

| Parvovirus copies/ml | SEQ ID NO: 17 Probe | SEQ ID NO: 27 Probe | SEQ ID NO: 28 Probe |
|---|---|---|---|
| 1,000 (positive control) | 273,238 ± 8,370<br>269,226 ± 9,517 | 232,836 ± 7,843<br>— | —<br>237,152 ± 7,482 |
| 10,000 | 282,473 ± 6,037<br>288,209 ± 5,299 | 258,127 ± 16,557<br>— | —<br>242,686 ± 13,025 |
| 5,000 | 283,015 ± 3,716<br>282,135 ± 14,676 | 245,047 ± 5,292<br>— | —<br>238,992 ± 3,790 |
| 1,000 | 263,795 ± 22,793<br>261,161 ± 13,038 | 241,110 ± 7,211<br>— | —<br>236,014 ± 6,581 |
| 500 | 224,858 ± 83,219<br>228,023 ± 50,281 | 216,921 ± 44,803<br>— | —<br>209,931 ± 49,130 |
| 250 | 167,216 ± 80,594<br>158,861 ± 100,765 | 138,291 ± 53,137<br>— | —<br>144,024 ± 75,550 |
| 100 | 84,296 ± 77,843<br>97,111 ± 97,430 | 79,058 ± 70,042<br>— | —<br>56,746 ± 42,133 |
| 50 | 39,551 ± 49,759<br>58,045 ± 83,433 | 30,533 ± 47,622<br>— | —<br>85,278 ± 101,652 |
| 25 | 16,403 ± 44,038<br>41,375 ± 72,116 | 1,526 ± 1,700<br>— | —<br>57,283 ± 91,578 |
| 0 (negative control) | 819 ± 232<br>786 ± 66 | 518 ± 55<br>— | —<br>512 ± 29 |
| NIBSC Standard | 157,522 ± 67,888<br>199,789 ± 68,636 | 97,318 ± 47,119<br>— | —<br>191,507 ± 51,276 |

The results showed that the three assay formats using different detection probes were substantially equivalent in their reactivity and sensitivity. That is, based on a positive signal of 30,000 or more detected RLU, all three formats detected 100 copies or more of parvovirus per ml of sample, and frequently detected fewer copies of parvovirus (25 and/or 50 copies/ml).

Example 5: Detection of Amplified Parvovirus Sequences Using Combinations of Detection Probes This example tested the sensitivity of the assay using individual detection probes or a mixture of two different detection probes. The mixture of detection probes contained equivalent amounts of probes of SEQ ID NO:27 and SEQ ID NO:28. Assays compared the detection probe mixture to use of either detection probe alone. The assays were performed substantially as described in Example 2, but using plasma samples that contained no parvovirus (negative control), or contained 500, 250, 100, 50, or 25 copies of parvovirus per ml; positive controls contained 1,000 copies/ml. Samples (1 ml) were assayed by first capturing the parvovirus DNA in a hybridization complex on magnetic particles using an oligomer having SEQ ID NO:1 with a 3' poly-A tail, as described above. Then, the parvovirus target sequence was amplified by using a one-hour TMA reaction that included a promoter primer of SEQ ID NO:23 and a primer of SEQ ID NO:13. The amplification products were detected by using detection probes of either SEQ ID NO:27 or SEQ ID NO:28 individually, or a mixture of probes of SEQ ID NO:27 and SEQ ID NO:28. The probes were labeled with 2-methyl-AE (between nt 5 and 6 for SEQ ID NO:27, and nt 9/10 for SEQ ID NO:28) and used at an activity of $1 \times 10^6$ RLU per reaction for each probe. For the positive and negative controls, five replicate samples were tested, whereas for each of the other experimental conditions, twenty replicate samples were tested. The results (RLU mean±standard deviation) are shown below.

TABLE 7

Detection Results Using Labeled Probes Alone or in Mixtures

| Parvovirus copies/ml | SEQ ID NO: 27 | SEQ ID NO: 28 | SEQ ID NO: 27 and SEQ ID NO: 28 |
|---|---|---|---|
| 1,000 (positive control) | 464,906 ± 10,157 | 476,397 ± 8,369 | 828,543 ± 31,127 |
| 500 | 412,338 ± 95,435 | 457,938 ± 34,499 | 679,652 ± 210,438 |
| 250 | 296,947 ± 179,021 | 397,804 ± 111,879 | 554,294 ± 272,640 |
| 100 | 167,560 ± 153,175 | 262,557 ± 189,262 | 376,880 ± 254,070 |
| 50 | 95,581 ± 145,780 | 70,364 ± 140,050 | 82,840 ± 145,301 |
| 0 (negative control) | 1,046 ± 205 | 826 ± 181 | 1,051 ± 116 |

The results show that both of the probes alone and in a mixture detected parvovirus at 500 copies/ml in all of the assays performed. Samples containing fewer copies of parvovirus were also detected (90 to 100% for 250 copies/ml, 75 to 85% for 100 copies/ml, and 30 to 50% for 50 copies/ml). The sensitivities of the three assay formats were substantially equivalent.

Example 6: Parvovirus Detection Using Differently Labeled Detection Probes

In this example, the amplified products produced using the method substantially as described in Example 5 were detected using various detection probe oligomers. The detection probe oligomers varied from one another either in their nucleotide sequence or, for probe oligomers with the same nucleotide sequence, at the position of label attachment to the oligomer. All of the probes were synthesized in vitro using standard chemical methods to produce an oligomer of specified sequence with a 2'-O-methoxy backbone. Oligomers were labeled with 2-methyl-AE as previously described (U.S. Pat. Nos. 5,585,481 and 5,639,604) using a linker compound to attach the label compound to the oligomer and used at an activity of 1×10.sup.6 RLU per reaction. The label position on the oligomer is referred to by the adjacent nucleotide positions, e.g., "12/13" means the linker and attached label are located between nt 12 and nt 13 of the oligomer. Detection probe oligomers tested in these experiments are summarized in Table 8.

The results of assays that used these detection probes are shown below, reported as the average (mean) RLU detected. Each probe was tested in five replicate assays of human plasma samples that contained no parvovirus DNA (negative samples) and plasma that contained 1,000 copies/ml of parvovirus (positive samples). The ratio of RLU detected in the positive samples to RLU detected in the negative samples (detection ratio) was determined using the average RLU results for each probe. (Table 9).

TABLE 9

Results Obtained By Using Differently Labeled Probes

| SEQ ID NO. and Label Position | Positive Samples (mean RLU) | Negative Samples (mean RLU) | Detection Ratio |
|---|---|---|---|
| NO: 27, Label 7/8 | 287,160 | 409 | 702 |
| NO: 27, Label 9/10 | 419,399 | 610 | 687 |
| NO: 27, Label 12/13 | 415,421 | 691 | 601 |
| NO: 27, Label 13/14 | 461,686 | 747 | 618 |
| NO: 28, Label 12/13 | 383,934 | 864 | 444 |
| NO: 30, Label 5/6 | 432,460 | 874 | 495 |
| NO: 30, Label 13/14 | 422,976 | 2,626 | 161 |
| NO: 31, Label 9/10 | 413,436 | 3,107 | 133 |
| NO: 31, Label 10/11 | 545,659 | 3,398 | 160 |
| NO: 32, Label 8/9 | 471,379 | 864 | 545 |
| NO: 32, Label 12/13 | 445,970 | 473 | 943 |
| NO: 34, Label 7/8 | 535,343 | 7,105 | 75 |
| NO: 34, Label 9/10 | 473,386 | 1,044 | 453 |
| NO: 34, Label 11/12 | 369,158 | 647 | 570 |
| NO: 34, Label 13/14 | 364,239 | 823 | 442 |
| NO: 34, Label 16/17 | 220,368 | 672 | 328 |
| NO: 34, Label 17/18 | 373,932 | 950 | 393 |
| NO: 36, Label 6/7 | 520,799 | 814 | 639 |

TABLE 8

Labeled Probes

| SEQ ID NO | Nucleotide Sequence | Label Positions |
|---|---|---|
| 27 | GTCATGGACAGTTATCTGAC | 7/8, 9/10, 12/13, and 13/14 |
| 28 | GTATTATCTAGTGAAGACTTAC | 12/13 |
| 30 | CTAGTGAAGACTTACACAAGC | 5/6 and 13/14 |
| 31 | GTGAAGACTTACACAAGCCTG | 9/10 and 10/11 |
| 32 | GCAGTATTATCTAGTGAAGAC | 8/9 and 12/13 |
| 34 | CAAAGTCATGGACAGTTATCTG | 7/8, 9/10, 11/12, 13/14, 16/17, and 17/18 |
| 36 | CTGTTTGACTTAGTTGCTCG | 6/7, 7/8, 10/11, 11/12, 14/15, and 15/16 |
| 37 | CTCTCCAGACTTATATAGTCATCAT | 7/8, 8/9, 9/10, 11/12, 12/13, 14/15, 16/17, 17/18, and 18/19 |

TABLE 9-continued

Results Obtained By Using Differently Labeled Probes

| SEQ ID NO. and Label Position | Positive Samples (mean RLU) | Negative Samples (mean RLU) | Detection Ratio |
|---|---|---|---|
| NO: 36, Label 7/8 | 482,847 | 792 | 609 |
| NO: 36, Label 10/11 | 370,929 | 633 | 586 |
| NO: 36, Label 11/12 | 343,754 | 757 | 454 |
| NO: 36, Label 14/15 | 364,239 | 823 | 442 |
| NO: 36, Label 15/16 | 382,139 | 1,016 | 376 |
| NO: 37, Label 7/8 | 336,293 | 61,020 | 5 |
| NO: 37, Label 8/9 | 81,986 | 1,314 | 62 |
| NO: 37, Label 9/10 | 516,495 | 57,853 | 9 |
| NO: 37, Label 11/12 | 559,173 | 133,530 | 4 |
| NO: 37, Label 12/13 | 506,083 | 121,133 | 4 |
| NO: 37, Label 14/15 | 593,889 | 54,116 | 5 |
| NO: 37, Label 16/17 | 439,755 | 94,380 | 4 |
| NO: 37, Label 17/18 | 361,001 | 91,163 | 4 |
| NO: 37, Label 18/19 | 222,039 | 2,233 | 99 |

The results showed that a variety of different detection probes may be used to detect parvovirus sequences in the amplification product because all of the probes tested produced at least four-fold more signal than the negative controls. Preferred embodiments generally have a detection ratio of 10 or greater. More preferably, the detection ratio is 100 or greater, and most preferably is in a range of 300 to 950. These results also showed that, for the same nucleotide sequence, the position of the label on the oligomer may influence the detection signal produced.

Example 7: Amplification and Detection Oligomers for Detecting Human Parvovirus Genotypes 1, 2 and 3

The object of this example was to amplify and detect human parvovirus genotypes 1, 2 and 3. Parvovirus nucleic acid sequences for genotypes 1, 2 and 3 were obtained from GenBank and were aligned using the Clustal W multiple sequence alignment algorithm. In a first amplification and detection assay, human parvovirus types 1-3 synthetic target nucleic acids were synthesized, (SEQ ID NO:91, SEQ ID NO:92 and SEQ ID NO:93, respectively). Twenty-five amplification oligomer combinations were designed and tested in an amplification and detection assay against 0, 10 or 1000 copies per reaction of these three synthetic targets. Amplification oligomer combinations included one or more of: a primer member (SEQ ID NOS:48 & 50); a tagged primer member (SEQ ID NOS:47 & 49); a T7 promoter primer (SEQ ID NOS:24, 56, 61, 76 & 81); and a T7 promoter primer with insert (SEQ ID NOS:58, 63, 68, 73 & 78). One or more inosine residues were substituted into SEQ ID NOS:73, 76, 78 & 81. Each positive condition was tested in triplicate, unless otherwise noted. Negative controls were run in duplicate. Reactive assays provided a signal to noise ratio of at least 10, calculated by dividing the average RLU value obtained from the reaction wells by the average RLU value obtained from the negative control wells. Systems providing a large standard deviation of RLU values under like conditions were considered to provide inconclusive results and are listed in the table as "undefined."

The combinations of amplification oligomers were prepared and each spiked into a primerless amplification reagent. These combinations were added to the reaction wells. A TMA amplification reaction was performed as substantially described above and was followed by a detection reaction. Detection of amplification product produced in the reaction wells, was achieved using a hybridization protection assay with SEQ ID NO:42 detection probe. Briefly, probe reagent was added to each reaction well, the detection reaction was incubated at 62.deg. C. for 15 minutes, selection reagent was added followed by a 10 minute and 62.deg. C. incubation and then a 10 minute room temp incubation. Detection results were obtained using a luminometer, RLUs were averaged and signal to noise ratios were calculated. A summary of the results is reported in Table 10 as "R"=reactive, "NR"=non-reactive, "Undef."=undefined, or "not tested." Signal-to-noise ratios are presented as "SN=v" where v is the calculated value, rounded to no decimal place.

TABLE 10

Detection Results Using Human Parvovirus Types 1, 2 and 3 Amplification and Detection Oligomers

| Amp Oligo Combos SEQ ID NOS | t1-1000 | t1-10 | t2-1000 | t2-10 | t3-1000 | t3-10 |
|---|---|---|---|---|---|---|
| 47 & 61 | NR (SN = 3) | NR (SN = 1) | NR (SN = 1) | NR (SN = 0) | NR (SN = 3) | NR (SN = 0) |
| 47 & 58 | R (SN = 437) | NR (SN = 1) | NR (SN = 4) | NR (SN = 3) | R (SN = 990) | NR (SN = 9) |
| 47, 56 & 23 | undef. | undef. | undef. | undef. | undef. | undef. |
| 47, 63 & 68 | R (SN = 542) | R (SN = 157) | R (SN = 232) | NR (SN = 1) | R (SN = 368) | NR (SN = 1) |
| 47, 76 & 81 | R (SN = 266) | NR (SN = 3) | R (SN = 271) | NR (SN = 1) | R (SN = 264) | NR (SN = 1) |
| 47, 73 & 78 | R (SN = 1427) | NR (SN = 1) | R (SN = 2041) | R (SN = 96) | R (SN = 1363) | R (SN = 1595) |
| 48 & 61 | NR (SN = 3) | NR (SN = 1) | NR (SN = 3) | NR (SN = 1) | NR (SN = 3) | NR (SN = 1) |
| 48 & 58 | NR (SN = 6) | NR (SN = 1) | NR (SN = 4) | NR (SN = 1) | R (SN = 21) | NR (SN = 1) |
| 48, 56 & 23 | undef. | undef. | undef. | undef. | undef. | undef. |
| 48, 63 & 68 | R (SN = 385) | NR (SN = 7) | R (SN = 47) | NR (SN = 1) | R (SN = 68) | NR (SN = 1) |
| 48, 76 & 81 | R (SN = 210) | R (SN = 27) | R (SN = 217) | NR (SN = 1) | R (SN = 215) | R (SN = 11) |
| 48, 73 & 78 | R (SN = 577) | NR (SN = 3) | R (SN = 583) | NR (SN = 3) | R (SN = 951) | R (SN = 68) |

TABLE 10-continued

Detection Results Using Human Parvovirus Types 1, 2 and 3 Amplification and Detection Oligomers

| Amp Oligo Combos SEQ ID NOS | t1-1000 | t1-10 | t2-1000 | t2-10 | t3-1000 | t3-10 |
|---|---|---|---|---|---|---|
| 48, 56 & 23 (re-test) | R (SN = 433) | not tested | R (SN = 214) | not tested | R (SN = 300) | not tested |
| 49 & 61 | NR (SN = 3) | NR (SN = 2) | NR (SN = 2) | NR (SN = 1) | NR (SN = 9) | NR (SN = 2) |
| 49 & 58 | NR (SN = 3) | NR (SN = 1) | NR (SN = 2) | NR (SN = 2) | NR (SN = 3) | NR (SN = 1) |
| 49, 56 & 23 | R (SN = 211) | undef. | NR (SN = 4) | NR (SN = 7) | R (SN = 290) | NR (SN = 1) |
| 49, 63 & 68 | R (SN = 338) | NR (SN = 2) | R (SN = 69) | NR (SN = 1) | R (SN = 120) | NR (SN = 4) |
| 49, 76 & 81 | R (SN = 112) | NR (SN = 1) | R (SN = 117) | NR (SN = 1) | NR (SN = 9) | NR (SN = 6) |
| 49, 73 & 78 | R (SN = 232) | R (SN = 26) | R (SN = 187) | NR (SN = 2) | R (SN = 374) | NR (SN = 3) |
| 50 & 61 | NR (SN = 3) | NR (SN = 1) | NR (SN = 2) | NR (SN = 1) | NR (SN = 3) | NR (SN = 1) |
| 50 & 58 | undef. | undef. | undef. | undef. | undef. | undef. |
| 50, 56 & 23 | R (SN = 516) | NR (SN = 1) | R (SN = 85) | NR (SN = 3) | R (SN = 508) | NR (SN = 2) |
| 50, 63 & 68 | R (SN = 208) | NR (SN = 1) | R (SN = 61) | NR (SN = 1) | R (SN = 36) | NR (SN = 1) |
| 50, 76 & 81 | R (SN = 219) | NR (SN = 1) | R (SN = 215) | R (SN = 72) | R (SN = 219) | NR (SN = 6) |
| 50, 73 & 78 | R (SN = 823) | NR (SN = 3) | R (SN = 1081) | NR (SN = 1) | R (SN = 1525) | R (SN = 16) |
| 50, 61 & 78* | R (SN = 578) | not tested | R (SN = 921) | not tested | R (SN = 1086) | not tested |

*five reaction wells tested

Sample wells providing RLU values at least 10-fold greater, and preferably at least 500-fold greater, than those provided by their corresponding negative control well are acceptable for a qualitative assay. Thus, a variety of the amplification oligomer combinations in this example detected the synthetic constructs representing parvovirus types 1, 2 and 3 target regions (SEQ ID NOS:91-93). The addition of a 5' tag sequence to SEQ ID NO:48 improved this primer member's performance when used with SEQ ID NO:61 promoter primer, but not when used with the SEQ ID NO:58 promoter primer. The use of two T7 promoter primer members in an amplification oligomer combination gave consistently good results at detecting 1000 copies of SEQ ID NO:91 per reaction. Similar results were seen with detection of 1000 copies of SEQ ID NOS:92 & 93, though not every combination produced a detectable product. Further, the substitution of a nucleotide residue with an inosine at mismatch sites resulted in amplification oligomer combinations with equivalent S:N, suggesting that the substitution provided similar amplification efficiencies. From the above data, SEQ ID NOS:50, 73, 78 were the selected amplification oligomer combination for continued testing.

Example 8: Qualitative TMA/HPA for the Detection of Parvovirus Types 1, 2 and 3

The objective of this example was to determine whether an amplification oligomer combination selected from Example 7 could detect human parvovirus from infected plasma samples. A further objective was to identify the end-point of detection using a blinded panel of plasma samples containing genotypes 1, 2 or 3 of parvovirus. The 2nd WHO International Standard (IS) for parvovirus DNA (IS 99/802, NIBSC)) was used as a positive control. The amplification oligomer combination used in this example was SEQ ID NOS:50, 73 & 78.

Target material was contained in five separate vials. One of the five vials was labeled 2nd WHO IS for B19V DNA (99/802) and contained the international standard for parvovirus (available from). The remaining four samples were each labeled #1, #2, #3 or #4, and each contained plasma infected with parvovirus, type 1, type 2, type 3 or contained uninfected plasma as determined by anti-b19 IgG and IgM. A first assay tested for the end-point of detection for the samples from a series of ten-fold dilutions. Starting from a thawed plasma sample, or, for IS 99/802, starting from a lyophilized sample reconstituted to 1 million IU/ml, a series of five ten-fold dilutions were prepared in order to determine (a) whether parvovirus DNA can be detected in the sample using the amplification oligomer combination, and (b) if detected, the dilution end point of that detection. Results are reported as positive (+) or negative (−) in Table 11. A second assay tested two half-log dilutions either side of the end-point determined in the first assay. Results are reported as positive (+) or negative (−) in Table 12.

Following preparation and dilution of the samples, each sample dilution was then mixed with lysing and capturing reagent containing SEQ ID NO:1 target capture oligomer comprising a dA30 3' tail. The mixture was incubated (60.deg. C., 20 min) to allow the capture oligomer to hybridize to any parvovirus target DNA in the sample. The mixtures further contained homopolymeric oligomers complementary to the 3'-tail portion of the capture oligomer and attached to magnetic particles. These homopolymeric complementary sequences hybridized in a second hybridization reaction (25.deg. C., 14-20 min) and the hybridization complexes that attached to the magnetic particles were separated from the rest of the sample and washed (e.g., twice with 1 ml of a buffer that maintains the hybridization complexes on the particles) before proceeding to amplification. After the samples were treated with the capture reagent, the magnetic particles with the attached hybridization complexes were incubated in an amplification mixture containing 15 pmol per reaction of each amplification oligomer member in the amplification oligomer combination SEQ ID NOS:50, 73 & 78, and the appropriate salts, nucleotides and enzymes for a one-hour TMA reaction (substantially as described in detail previously in U.S. Pat. Nos. 5,399,491 and 5,554,516). The detection probe of SEQ ID NO:42 labeled between residues 9 and 10 with 2-methyl-AE was added (0.1 pmol per reaction) and incubated (60.deg. C., 20 min) with the amplification products to allow hybridization. Chemiluminescent signal was detected (RLU) as described in detail previously (U.S. Pat. Nos. 5,283,174, 5,656,207, and 5,658,737). Results are presented in Tables 11-12. Though a S:N of 10 is useful, higher S:N are preferred. here, reaction wells resulting in a S:N value of at least 30 were determined to be reactive. (+)=Reactive; (−)=Not Reactive; (NT)=Not Tested.

TABLE 11

First Estimation of End-Point

| | | Dilution | | | | | | |
|---|---|---|---|---|---|---|---|---|
| | Stock | 10.sup.-1 | 10.sup.-2 | 10.sup.-3 | 10.sup.-4 | 10.sup.-5 | 10.sup.-6 | 10.sup.-7 |
| IS (99/802) | NT | + | + | + | − | − | − | NT |
| #1 | NT | + | + | + | − | − | − | NT |
| #2 | NT | + | + | + | − | + | − | NT |
| #3 | NT | + | + | − | − | − | − | NT |
| #4 | NT | − | − | − | − | − | − | NT |

TABLE 12

Second Estimation of End-Point

| | Dilution +/− | | | | |
|---|---|---|---|---|---|
| #1 | 10.sup.-3 | 10.sup.-3.5 | 10.sup.-4 | 10.sup.-4.5 | 10.sup.-5 |
| | + | + | − | − | − |
| | + | + | + | − | − |
| | + | − | + | − | − |
| #2 | 10.sup.-4 | 10.sup.-4.5 | 10.sup.-5 | 10.sup.-5.5 | 10.sup.-6 |
| | + | + | − | − | − |
| | + | + | + | − | − |
| | + | − | − | − | − |
| #3 | 10.sup.-2 | 10.sup.-2.5 | 10.sup.-3 | 10.sup.-3.5 | 10.sup.-4 |
| | + | + | + | − | − |
| | + | + | + | − | − |
| | + | + | + | − | − |
| #4 | 0 | 10.sup.-0.5 | 10.sup.-1 | 10.sup.-1.5 | 10.sup.-2 |
| | − | − | − | − | − |
| | − | − | − | − | − |
| | − | − | − | − | − |
| IC (99/802) | 10.sup.-3 | 10.sup.-3.5 | 10.sup.-4 | 10.sup.-4.5 | 10.sup.-5 |
| | + | + | + | − | − |
| | + | + | + | + | − |
| | + | + | − | − | − |

Parvovirus DNA was detected in each of samples #1, #2 and #3 as well as in the IC positive control sample. No parvovirus was detected in sample #4, indicating that this sample was the negative control. Samples #1, #2 and #3 were then sequenced and sequencing confirmed that these samples contained a parvovirus genotype 1, 2 or 3, respectively. Thus, parvovirus genotypes 1, 2 and 3 were detected from plasma samples.

Example 9: Detection of Parvovirus Types 1, 2 and 3

The object of this example is to test different amplification oligomer combinations for their ability to amplify types 1, 2 and 3 parvovirus DNA. In this example, a first amplification oligomer combination comprised SEQ ID NOS:13, 51, 23 and 56. SEQ ID NOS:13 and 23 are a nonT7 primer and a T7 promoter primer, respectively, are described in Examples 3-6, and have been shown to produce detectable amplicons from samples containing human parvovirus. SEQ ID NOS: 51 and 56 are a nonT7 primer and a T7 promoter primer, respectively, and are also present in this first amplification oligomer combination. SEQ ID NO:56 comprises a target binding domain (SEQ ID NO:57) and a T7 RNA polymerase promoter sequence (SEQ ID NO:19). A second amplification oligomer combination comprised SEQ ID NOS:47, 73 & 78. Within this second amplification oligomer design are two T7 promoter primers, SEQ ID NO:73 and SEQ ID NO:78. SEQ ID NO:73 comprises a target binding domain (SEQ ID NO:75), an insert tag sequence (SEQ ID NO:94), an inosine residue (n=I) and an RNA polymerase region (SEQ ID NO:19). SEQ ID NO:78 comprises a target binding domain (SEQ ID NO:80), as well as an insert tag sequence (SEQ ID NO:94), two inosine residues (n=I) and an RNA polymerase region (SEQ ID NO:19). Also within the second amplification oligomer combination is a nonT7 primer comprising a target binding domain (SEQ ID NO:48) and a 5'tag sequence (SEQ ID NO:95).

Target material was the same as that used in Example 8; namely, IS 99/802, sample #1, sample #2, sample #3 and sample #4. The target capture oligomer used with both amplification oligomer combination configurations was SEQ ID NO:53. The detection oligomer used with both amplification oligomer combination configurations was SEQ ID NO:42. Samples were serially diluted and each dilution was mixed with lysing and capturing reagent containing SEQ ID NO:53, as described above. Captured target were then incubated in amplification mixtures containing the first or the second amplification oligomer combination, followed by chemiluminescent detection. Results are presented in Tables 13-14

TABLE 13

Amplification Oligomer Combination Performance - 10-Fold Dilutions

| | SEQ ID NOS: 13, 51, 23 and 56 | SEQ ID NOS: 47, 73 and 78 |
|---|---|---|
| | S/Co | S/Co |
| IS 99/802 10.sup.-2 | 25.58 | 32.37 |
| IS 99/802 10.sup.-3 | 11.04 | 33.47 |
| IS 99/802 10.sup.-4 | 0.35 | 0.00 |
| Sample #1 10.sup.-2 | 26.28 | 34.32 |
| Sample #2 10.sup.-2 | 4.48 | 34.26 |
| Sample #3 10.sup.-2 | 1.85 | 26.14 |

TABLE 14

Amplification Oligomer Combination Performance - Half-log Dilutions

| | SEQ ID NOS: 13, 51, 23 and 56 Average S/Co | SEQ ID NOS: 47, 73 and 78 Average S/Co |
|---|---|---|
| IS 99/802 10.sup.-3 | 6.34 | 31.03 |
| IS 99/802 10.sup.-3.5 | 2.60 | 18.69 |
| IS 99/802 10.sup.-4 | 0.24 | 10.80 |
| IS 99/802 10.sup.-4.5 | 0.28 | 2.63 |
| IS 99/802 10.sup.-5 | 0.18 | 0.04 |
| Sample #1 10.sup.-3 | 8.56 | 29.34 |
| Sample #1 10.sup.-3.5 | 5.78 | 9.31 |
| Sample #1 10.sup.-4 | 0.28 | 11.13 |
| Sample #1 10.sup.-4.5 | 0.44 | 0.10 |
| Sample5 #1 10.sup.-5 | 0.22 | 0.06 |
| Sample #2 10.sup.-3 | 0.26 | 10.53 |
| Sample #2 10.sup.-3.5 | 0.29 | 14.70 |
| Sample #2 10.sup.-4 | 0.25 | 2.20 |
| Sample #2 10.sup.-4.5 | 0.14 | 0.05 |
| Sample #2 10.sup.-5 | 0.11 | 0.37 |
| Sample #3 10.sup.-3 | 1.89 | 23.60 |
| Sample #3 10.sup.-3.5 | 0.73 | 23.06 |
| Sample #3 10.sup.-4 | 0.36 | 17.99 |
| Sample #3 10.sup.-4.5 | 0.24 | 0.26 |
| Sample #3 10.sup.-5 | 0.38 | 0.09 |

In this example, these data showed that the amplification oligomer combination SEQ ID NOS:47, 73 and 78 detected human parvovirus types 1, 2 and 3 with a sensitivity to about 100 copies. These data also show that the SEQ ID NOS:47, 73 and 78 amplification oligomer combination detected parvovirus genotype 1 with better sensitivity than did the SEQ ID NOS:13, 51, 23 and 56 amplification oligomer combination. These data also showed that the SEQ ID NOS:47, 73 and 78 amplification oligomer combination detected types 2 and 3 parvovirus, while the SEQ ID NOS:13, 51, 23 and 56 amplification oligomer combination did not.

TABLE 15

Exemplary Oligomers, Reference Sequences and Regions

| SEQ ID NO: | Sequence (5' to 3') | |
|---|---|---|
| 1 | gttggctatacctaaagtcatgaatcct | TCO. [TBS] only. |
| 2 | gccagttggctatacctaaagtcatgaatcct | TCO. [TBS] only. |
| 3 | aatttaatacgactcactatagggagacta ggttctgcatgactgctactgga | T7. [PRO/SEQ ID NO: 19] + [TBS/SEQ ID NO: 4]. |
| 4 | ctaggttctgcatgactgctactgga | T7. [TBS] only. |
| 5 | aatttaatacgactcactatagggagactg catgactgctactggatgataag | T7. [PRO/SEQ ID NO: 19] + [TBS/SEQ ID NO: 6]. |
| 6 | ctgcatgactgctactggatgataag | T7. [TBS] only. |
| 7 | aatttaatacgactcactatagggagacta ggttctgcatgactgctactggatga | T7. [PRO/SEQ ID NO: 19] + [TBS/SEQ ID NO: 8]. |
| 8 | ctaggttctgcatgactgctactggatga | T7. [TBS] only. |
| 9 | aatttaatacgactcactatagggagagtt ctgcatgactgctactggatga | T7. [PRO/SEQ ID NO: 19] + [TBS/SEQ ID NO: 10]. |
| 10 | gttctgcatgactgctactggatga | T7. [TBS] only. |
| 11 | aatttaatacgactcactatagggagattc tcctctaggttctgcatgactgc | T7. [PRO/SEQ ID NO: 19] + [TBS/SEQ ID NO: 12]. |
| 12 | ttctcctctaggttcttgcatgactgc | T7. [TBS] only. |
| 13 | cccctagaaaacccatcctct | Primer. [TBS] only. |
| 14 | ctctccagacttatatagtcatcattttc | Primer. [TBS] only. |
| 15 | ctctccagacttatatagtcatcat | Primer. [TBS] only. |
| 16 | atccctagaaaacccatcctct | Primer. [TBS] only. |
| 17 | gacagttatctgaccaccccatgc | Probe. [TBS] only. |
| 18 | catggacagttatctgaccacc | Probe. [TBS] only. |
| 19 | aatttaatacgactcactatagggaga | Probe. [TBS] only. |
| 20 | catcactttcccaccatttgccacttt | TCO. [TBS] only. |

TABLE 15-continued

Exemplary Oligomers, Reference Sequences and Regions

| SEQ ID NO: | Sequence (5' to 3') | |
|---|---|---|
| 21 | gcaaatttatcatcactttcccaccatttgcc | TCO. [TBS] only. |
| 22 | aggattcatgactttaggtatagccaac | Region. |
| 23 | aatttaatacgactcactatagggagaagtaccgggtagttgtacgctaact | T7. [PRO/SEQ ID NO: 19] + [TBS/SEQ ID NO: 24]. |
| 24 | agtaccgggtagttgtacgctaact | T7. [TBS] only. |
| 25 | cttatcatccagtaacagtcatgcagaacctagaggagaaaatgcagtattatctagtgaagacttacacaagcctgggcaa | TSS corresponding to residues 2333-2414 of SEQ ID NO: 90. |
| 26 | gacagttatctgaccaccccatgccttatcatccagtaacagtcatgcagaacctagaggagaaaatgcagtattatctagtgaagacttacacaagcctgggcaa | TSS corresponding to residues 2308 to 2414 of SEQ ID NO: 90. |
| 27 | gtcatggacagttatctgac | Probe. [TBS] only. |
| 28 | gtattatctagtgaagacttac | Probe. [TBS] only. |
| 29 | aaagtggcaaatggtgggaaagtgatgataaatttgc | Region. |
| 30 | ctagtgaagacttacacaagc | Probe. [TBS] only. |
| 31 | gtgaagacttacacaagcctg | Probe. [TBS] only. |
| 32 | gcagtattatctagtgaagac | Probe. [TBS] only. |
| 33 | gcagtattatctagtgaagacttacacaagcctg | Region. |
| 34 | CAAAGUCAUGGACAGUUAUCUG | Probe. [TBS] only. |
| 35 | caaagtcatggacagttatctgaccaccccatgc | Region. |
| 36 | ctgtttgacttagttgctcg | Probe. [TBS] only. |
| 37 | cucuccagacuuauauagucaucau | Probe. [TBS] only. |
| 38 | gtcatggacagttatctg | Region. |
| 39 | gtgaagacttacacaagc | TSS corresponding to residues 2389-2406 of SEQ ID NO: 90. |
| 40 | gtattatctagtgaagac | Region. |
| 41 | catcactttcccaccatttgcc | Portion of Capture probe TBS. |
| 42 | GUAUUAUCUAGUGAAGACUUAC | Probe. [TBS] only. |
| 43 | CUAGUGAAGACUUACACAAGC | Probe. [TBS] only. |
| 44 | GUGAAGACUUACACAAGCCUG | Probe. [TBS] only. |
| 45 | caaagtcatggacagttatctg | Probe. [TBS] only. |
| 46 | GCAGUAUUAUCUAGUGAAGAC | Probe. [TBS] only. |
| 47 | GTCATATGCGACGATCTCAGGACAGTTATCTGACCACCCCCATGC | Primer. [Taq/SEQ ID NO: 95] + [TBS/SEQ ID NO: 48]. |
| 48 | GACAGTTATCTGACCACCCCCATGC | Primer. [TBS] only. |
| 49 | GTCATATGCGACGATCTCAGGACAGTTATCTGACCACC | Primer. [Taq/SEQ ID NO: 95] + [TBS/SEQ ID NO: 50]. |
| 50 | GACAGTTATCTGACCACC | Primer. [TBS] only. |

TABLE 15-continued

Exemplary Oligomers, Reference Sequences and Regions

SEQ ID NO: Sequence (5' to 3')

| SEQ ID NO | Sequence | Description |
|---|---|---|
| 51 | TCTCTGTTTGACTTAGTTGCTCG | Primer. [TBS] only. |
| 52 | ggttggctatacctaaagtcatgaatcctt ttaaaaaaaaaaaaaaaaaaaaaaaaaa aa | TCO. [TBS/SEQ ID NO: 53] + [dT3/dA30]. |
| 53 | ggttggctatacctaaagtcatgaatcct | TCO. [TBS] only. |
| 54 | gucauggacaguuaucugac | Probe. [TBS] only. |
| 55 | GenBank Accession No. DQ234772.1 GI: 78217253, entered Nov. 2, 2005. | |
| 56 | AATTTAATACGACTCACTATAGGGAGACCA ACATAGTTAGTACCGGGTAGTTG | T7. [PRO/SEQ ID NO: 19] + [TBS/SEQ ID NO: 57]. |
| 57 | CCAACATAGTTAGTACCGGGTAGTTG | T7. [TBS] only. |
| 58 | AATTTAATACGACTCACTATAGGGAGACCT ACGATGCATCCAACATAGTTAGTACCGGGT A | T7. [PRO/SEQ ID NO: 19] + [Insert/SEQ ID NO: 94] + [TBS/SEQ ID NO: 60]. |
| 59 | CCTACGATGCATCCAACATAGTTAGTACCG GGTA | T7. [Insert/SEQ ID NO: 94] + [TBS/SEQ ID NO: 60]. |
| 60 | CCAACATAGTTAGTACCGGGTA | T7. [TBS] only. |
| 61 | AATTTAATACGACTCACTATAGGGAGACCA ACATAGTTAGTACCGGGTA | T7. [PRO/SEQ ID NO: 19] + [TBS/SEQ ID NO: 60]. |
| 62 | CCAACATAGTTAGTACCGGGTARTTG | T7. [TBS] only. |
| 63 | AATTTAATACGACTCACTATAGGGAGACCT ACGATGCATCCAACATAGTTAGTACCGGGT AGTTG | T7. [PRO/SEQ ID NO: 19] + [Insert/SEQ ID NO: 94] + [TBS/SEQ ID NO: 57]. |
| 64 | CCTACGATGCATCCAACATAGTTAGTACCG GGTAGTTG | T7. [Insert/SEQ ID NO: 94] + [TBS/SEQ ID NO: 57]. |
| 65 | CCTACGATGCATCCAACATAGTTAGTACCG GGTARTTG | T7. [Insert/SEQ ID NO: 94] + [TBS/SEQ ID NO: 62]. |
| 66 | AATTTAATACGACTCACTATAGGGAGACCA ACATAGTTAGTACCGGGTARTTG | T7. [PRO/SEQ ID NO: 19] + [TBS/SEQ ID NO: 62]. |
| 67 | AATTTAATACGACTCACTATAGGGAGACCT ACGATGCATCCAACATAGTTAGTACCGGGT ARTTG | T7. [PRO/SEQ ID NO: 19] + [Insert/SEQ ID NO: 94] + [TBS/SEQ ID NO: 62]. |
| 68 | AATTTAATACGACTCACTATAGGGAGACCT ACGATGCATAGTACCGGGTAGTTGTACGCT AACT | T7. [PRO/SEQ ID NO: 19] + [Insert/SEQ ID NO: 94] + [TBS/SEQ ID NO: 24]. |
| 69 | CCTACGATGCATAGTACCGGGTAGTTGTAC GCTAACT | T7. [Insert/SEQ ID NO: 94] + [TBS/SEQ ID NO: 24]. |
| 70 | agtaccgggtaRttgtaYgctaact | T7. [TBS] only. |
| 71 | CCTACGATGCATagtaccgggtaRttgtaY gctaact | T7. [Insert/SEQ ID NO: 94] + [TBS/SEQ ID NO: 70]. |
| 72 | AATTTAATACGACTCACTATAGGGAGAagt accgggtaRttgtaYgctaact | T7. [PRO/SEQ ID NO: 19] + [TBS/SEQ ID NO: 70]. |
| 73 | AATTTAATACGACTCACTATAGGGAGACCT ACGATGCATCCAACATAGTTAGTACCGGGT AnTTG | T7. [PRO/SEQ ID NO: 19] + [Insert/SEQ ID NO: 94] + [TBS/SEQ ID NO: 75]. |
| 74 | CCTACGATGCATCCAACATAGTTAGTACCG GGTAnTTG | T7. [Insert/SEQ ID NO: 94] + [TBS/SEQ ID NO: 75]. |
| 75 | CCAACATAGTTAGTACCGGGTAnTTG | T7. [TBS] only. |
| 76 | AATTTAATACGACTCACTATAGGGAGACCA ACATAGTTAGTACCGGGTAnTTG | T7. [PRO/SEQ ID NO: 19] + [TBS/SEQ ID NO: 75]. |

TABLE 15-continued

Exemplary Oligomers, Reference Sequences and Regions

| SEQ ID NO: | Sequence (5' to 3') | |
|---|---|---|
| 77 | GenBank Accession No.: DQ333428.1 GI: 84180808, entered Jan. 8, 2006 with non-sequences updates on Dec. 20, 2007. | |
| 78 | AATTTAATACGACTCACTATAGGGAGACCT ACGATGCATAGTACCGGGTAnTTGTAnGCT AACT | T7. [PRO/SEQ ID NO: 19] + [Insert/SEQ ID NO: 94] + [TBS/SEQ ID NO: 80]. |
| 79 | CCTACGATGCATAGTACCGGGTAnTTGTAn GCTAACT | T7. [Insert/SEQ ID NO: 94] + [TBS/SEQ ID NO: 80]. |
| 80 | AGTACCGGGTAnTTGTAnGCTAACT | T7. [TBS] only. |
| 81 | AATTTAATACGACTCACTATAGGGAGAAGT ACCGGGTAnTTGTAnGCTAACT | T7. [PRO/SEQ ID NO: 19] + [TBS/SEQ ID NO: 80]. |
| 82 | AATTTAATACGACTCACTATAGGGAGACCT ACGATGCATagtaccgggtaRttgtaYgct aact | T7. [PRO/SEQ ID NO: 19] + [Insert/SEQ ID NO: 94] + [TBS/SEQ ID NO: 70]. |
| 83 | TACCCGGTACT | Region. |
| 84 | CAAnTACCCGGTACT | Portion of T7 TBS. |
| 85 | AGTTAGCGTACAACTACCCGGTACTAACTA TGTTGG | Region. |
| 86 | gcagtattatctagtgaagacttacacaag cctgggcaa | TSS corresponding to residues 2376-2414 of SEQ ID NO: 90. |
| 87 | catggacagttatctgaccaccccccatggc ttatcatccagtaacagtcatgcagaacct agaggagaaaatgcagtattatctagtgaa gacttacacaagcctg | TSS corresponding to residues 2304-2409 of SEQ ID NO: 90. |
| 88 | catggacagttatctgaccaccccccatgcc ttatcatccagtaacagtcatgcagaacct agaggagaaaatgcagtattatctagtgaa gacttacacaagcctgggcaagttagcgta caactacccggtactaactatgttgg | TSS corresponding to residues 2304-2449 of SEQ ID NO: 90. |
| 89 | cttatcatccagtaacagtcatgcagaacc tagaggagaaaatgcagtattatctagtga agacttacacaagcctgggcaagttagcgt acaactacccggtact | TSS corresponding to residues 2333-2438 of SEQ ID NO: 90. |
| 90 | GenBank Accession No. DQ225149.1 GI: 77994407, entered Oct. 26, 2005, with non-sequence updates on Sep. 12, 2006. | |
| 91 | AGTCATGGACAGTTATCTGACCACCCCCAT GCCTTATCATCCAGTAGCAGTCATGCAGAA CCTAGAGGAGAAAATGCAGTATTATCTAGT GAAGACTTACACAAGCCTGGGCAAGTTAGC GTACAACTACCCGGTACTAACTATGTTGGG CCTGGCAATGAGCTACAAGCTG | Type 1 synthetic construct. |
| 92 | AGTCATGGACAGTTATCTGACCACCCCCAT GCCTTATCACCCAGTAGCAGTCATACAGAA CCTAGAGGAGAAAATGCAGTATTATCTAGT GAAGACTTACACAAGCCTGGGCAAGTTAGC ATACAACTACCCGGTACTAACTATGTTGGG CCTGGCAATGAGCTACAAGCTG | Type 2 synthetic construct. |
| 93 | AGCCATGGACAGTTATCTGACCACCCCCAT GCCTTATCACCCAGTAACAGTAGTACAGAA CCTAGAGGAGAAAATGCAGTATTATCTAGT GAAGACTTACACAAGCCTGGGCAAGTTAGC ATACAATTACCCGGTACTAACTATGTTGGG CCTGGCAATGAGCTACAAGCTG | Type 3 synthetic construct. |
| 94 | CCTACGATGCAT | Insert sequence |
| 95 | GTCATATGCGACGATCTCAG | Tag sequence |
| 96 | catggacagttatctgaccaccccccatgc | Region. |

TABLE 15-continued

Exemplary Oligomers, Reference Sequences and Regions

| SEQ ID NO: | Sequence (5' to 3') | |
|---|---|---|
| 97 | tacccggtactaactatgttgg | Region. |
| 98 | cttatcatccagtaacagtcatgcagaacc tagaggagaaaatgcagtattatctagtga agacttacacaagcctg | TSS corresponding to residues 2333-2409 of SEQ ID NO: 90. |
| 99 | gcagtattatctagtgaagacttacacaag cctgggcaagttagcgtacaactacccggt act | TSS corresponding to residues 2376-2438 of SEQ ID NO: 90. |
| 100 | gacagttatctgaccaccccatgccttat catccagtaacagtcatgcagaacctagag gagaaaatgcagtattatctagtgaagact tacacaagcctgggcaagttagcgtacaac tacccggtact | TSS corresponding to residues 2308-2438 of SEQ ID NO: 90. |

Legend: TCO = Target Capture Oligomer. TBS = Target Binding Sequence. TSS = Target Specific Sequence. T7 = promoter based amplification oligomer. Primer = Primer amplification oligomer. Probe = Detection probe oligomer.

The present invention has been described in the context of particular examples and preferred embodiments. Those skilled in the art will appreciate that other embodiments are encompassed within the invention defined by the claims that follow.

---

I claim:

1. A method for the detection of human parvovirus from a sample comprising the steps of:
   a) obtaining a sample suspected of containing human parvovirus genotype 1, genotype 2, or genotype 3;
   b) contacting the sample with an amplification oligomer combination comprising:
      i) at least one primer oligomer member comprising a target-binding sequence that is SEQ ID NO:48 or SEQ ID NO:50;
      ii) a first promoter-based oligomer member that is SEQ ID NO:73; and
      iii) a second promoter-based oligomer member that is SEQ ID NO:78;
   c) performing an isothermal amplification reaction on the sample to generate an amplicon from a human parvovirus in the sample or from an amplicon thereof; and
   d) detecting the amplicon with a detection probe oligomer; wherein the presence of an amplicon as determined by the detecting step indicates that one or more of human parvovirus genotypes 1, 2 and 3 are present in the sample.

2. The method of claim 1, wherein the at least one primer oligomer member comprises the target-binding sequence that is SEQ ID NO:50.

3. The method of claim 1, wherein the at least one primer oligomer member comprises the target-binding sequence that is SEQ ID NO:48.

4. The method of claim 3, wherein the at least one primer oligomer member is SEQ ID NO:47.

5. The method of claim 1, wherein the at least one primer oligomer member comprises a 5' tag sequence.

6. The method of claim 1, wherein the at least one primer member is selected from the group consisting of SEQ ID NO:47, SEQ ID NO:48, SEQ ID NO:49, SEQ ID NO:50, and combinations thereof.

7. The method of claim 1, wherein the detection probe oligomer is selected from the group consisting of SEQ ID NO:28, SEQ ID NO:30, SEQ ID NO:31, SEQ ID NO:32, SEQ ID NO:42, SEQ ID NO:43, SEQ ID NO:44, and SEQ ID NO:46.

8. The method of claim 1, further comprising the step of contacting the sample with a target capture oligomer.

9. The method of claim 8, wherein the target capture oligomer comprises a 3' tail portion and a target-binding sequence selected from the group consisting of SEQ ID NO:1, SEQ ID NO:2, SEQ ID NO:20, SEQ ID NO:21, SEQ ID NO:53, and combinations thereof.

10. The method of claim 9, wherein the target capture oligomer is SEQ ID NO:52.

11. A method for the detection of human parvovirus from a sample comprising the steps of:
   a) obtaining a sample suspected of containing human parvovirus genotype 1, genotype 2, or genotype 3;
   b) contacting the sample with an amplification oligomer combination comprising at least one primer oligomer member and at least one promoter-based oligomer member, wherein the at least one primer oligomer member and the at least one promoter-based oligomer member hybridize to opposing strands of a human parvovirus genotype 1, 2 or 3 nucleic acid or amplicon thereof for transcription mediated amplification of the target nucleic acid or amplicon thereof between the hybridized primer and promoter-based oligomer members, wherein the at least one promoter-based oligomer member is a first promoter-based oligomer member that is SEQ ID NO:76 and a second promoter-based oligomer member that is SEQ ID NO:81;
   c) performing an isothermal amplification reaction on the sample to generate an amplicon from a human parvovirus in the sample or from an amplicon thereof; and
   d) detecting the amplicon with a detection probe oligomer; wherein the presence of an amplicon as determined by the detecting step indicates that one or more of human parvovirus genotypes 1, 2 and 3 are present in the sample.

12. The method of claim 11, wherein the detection probe oligomer is selected from the group consisting of SEQ ID NO:28, SEQ ID NO:30, SEQ ID NO:31, SEQ ID NO:32, SEQ ID NO:42, SEQ ID NO:43, SEQ ID NO:44, and SEQ ID NO:46.

13. The method of claim 11, further comprising the step of contacting the sample with a target capture oligomer.

14. The method of claim 13, wherein the target capture oligomer comprises a 3' tail portion and a target-binding sequence selected from the group consisting of SEQ ID NO:1, SEQ ID NO:2, SEQ ID NO:20, SEQ ID NO:21, SEQ ID NO:53, and combinations thereof.

15. A method for the detection of human parvovirus from a sample comprising the steps of:
   a) obtaining a sample suspected of containing human parvovirus genotype 1, genotype 2, or genotype 3;
   b) contacting the sample with an amplification oligomer combination comprising at least one primer oligomer member and at least one promoter-based oligomer member, wherein the at least one primer oligomer member and the at least one promoter-based oligomer member hybridize to opposing strands of a human parvovirus genotype 1, 2 or 3 nucleic acid or amplicon thereof for transcription mediated amplification of the target nucleic acid or amplicon thereof between the hybridized primer and promoter-based oligomer members, wherein
      i) the at least one promoter-based oligomer member is selected from the group consisting of SEQ ID NOS: 58, 63, 67, 68, 73, 78, 82, and combinations thereof; or
      ii) the at least one primer oligomer member is SEQ ID NO:47 and the at least one promoter-based oligomer member is selected from the group consisting of SEQ ID NOs:73, 76, 78, 81, and combinations thereof;
   c) performing an isothermal amplification reaction on the sample to generate an amplicon from a human parvovirus in the sample or from an amplicon thereof; and
   d) detecting the amplicon with a detection probe oligomer; wherein the presence of an amplicon as determined by the detecting step indicates that one or more of human parvovirus genotypes 1, 2 and 3 are present in the sample.

16. The method of claim 15, wherein the detection probe oligomer is selected from the group consisting of SEQ ID NO:28, SEQ ID NO:30, SEQ ID NO:31, SEQ ID NO:32, SEQ ID NO:42, SEQ ID NO:43, SEQ ID NO:44, and SEQ ID NO:46.

17. The method of claim 15, further comprising the step of contacting the sample with a target capture oligomer.

18. The method of claim 17, wherein the target capture oligomer comprises a 3' tail portion and a target-binding sequence selected from the group consisting of SEQ ID NO:1, SEQ ID NO:2, SEQ ID NO:20, SEQ ID NO:21, SEQ ID NO:53, and combinations thereof.

19. A method for the detection of human parvovirus from a sample comprising the steps of:
- a) obtaining a sample suspected of containing human parvovirus genotype 1, genotype 2, or genotype 3;
- b) contacting the sample with an amplification oligomer combination comprising:
  - i) at least one primer oligomer member that is SEQ ID NO:47;
  - ii) a first promoter-based oligomer member comprising a target binding sequence that is SEQ ID NO:75; and
  - iii) a second promoter-based oligomer member comprising a target binding sequence that is SEQ ID NO:80;

wherein the target binding sequence of each of the first and second promoter-based oligomer members is joined at its 5' end to a promoter sequence;
- c) performing an isothermal amplification reaction on the sample to generate an amplicon from a human parvovirus in the sample or from an amplicon thereof; and
- d) detecting the amplicon with a detection probe oligomer; wherein the presence of an amplicon as determined by the detecting step indicates that one or more of human parvovirus genotypes 1, 2 and 3 are present in the sample.

* * * * *